(12) United States Patent
Horibe et al.

(10) Patent No.: US 6,200,929 B1
(45) Date of Patent: Mar. 13, 2001

(54) CROP-SELECTIVE HERBICIDE

(75) Inventors: Yoshimichi Horibe, Hikone; Tadashi Amagasa, Yokohama; Kazuo Sato, Hikone; Takahiro Tsukiyama, Shiga-ken, all of (JP)

(73) Assignee: Sankyo Company, Limited, Tokyo (JP)

( * ) Notice: Subject to any disclaimer, the term of this patent is extended or adjusted under 35 U.S.C. 154(b) by 0 days.

(21) Appl. No.: 09/296,825

(22) Filed: Apr. 22, 1999

Related U.S. Application Data

(63) Continuation of application No. PCT/JP97/04031, filed on Nov. 6, 1997.

(30) Foreign Application Priority Data

| Nov. 7, 1996 | (JP) | 8-294835 |
| Nov. 14, 1996 | (JP) | 8-303039 |
| Jan. 30, 1997 | (JP) | 9-015794 |

(51) Int. Cl.$^7$ ................................................. A01N 57/02
(52) U.S. Cl. ........................ 504/127; 504/128; 504/206
(58) Field of Search ................................. 504/206, 127, 504/128

(56) References Cited

U.S. PATENT DOCUMENTS

| 3,853,530 | 12/1974 | Franz | 71/76 |
| 4,657,581 | * 4/1987 | Takematsu et al. | 71/118 |
| 5,656,572 | * 8/1997 | Kuchikata et al. | 504/206 |

FOREIGN PATENT DOCUMENTS

| 109314 | 5/1984 | (EP) . |
| 431545 | 6/1991 | (EP) . |

OTHER PUBLICATIONS

John D. Nalewaja and Robert Matysiak, "Salt Antagonism of Glyphosate", Weed Science, *39*, 622–628 (1991).

* cited by examiner

*Primary Examiner*—S. Mark Clardy
(74) *Attorney, Agent, or Firm*—Frishauf, Holtz, Goodman, Langer & Chick, P.C.

(57) ABSTRACT

An agricultural chemical composition which comprises a first component having herbicidal activity selected from the group consisting of glyphosate and the like and a second component selected from the group consisting of phosphorus acid derivatives and the like and may further comprise a third component selected from maleic hydrazide and the like; and use of it as a plant growth retardant and crop selective herbicide.

50 Claims, No Drawings

CROP-SELECTIVE HERBICIDE

This application is a continuation application of International Application PCT/JP97/04031 filed Nov. 6, 1997.

TECHNICAL FIELD

The present invention relates to an agricultural chemical composition which comprises one or more than one first component having herbicidal activity selected from nonselective phosphoric acid herbicides (group a) and one or more than one second component selected from phosphorus acid derivatives and the like (group b) and optionally one or more than one third component selected from maleic hydrazide and the like (group c); and the use of said composition as a plant growth retardant or crop selective herbicide.

BACKGROUND OF THE INVENTION

If weeds are allowed to grow in a place such as a railroad, superhighway, open space left as it is, factory site, bank, levee between rice fields, orchard, or unplowed paddy or field, they presumably exert various bad influences on the place, for example, disturb the visibility of transportation, become a source of generation of disease and insect damage or interfere with farm work. In consideration of recent shortage in labor and increase in the labor cost, it has been difficult to control such weed growth, depending only on the human power and machine and it has been important to use a nonselective herbicide such as glyphosate, glyphosine, bialaphos or glufosinate.

When a lethal amount of the above-described nonselective herbicide is employed on the face of a slope or a levee between rice fields, however, it destroys almost all the weeds and no plant is left on the surface of soil, which leads to a problem of an outflow of the soil. In such a place, there is accordingly a demand for an agent that does not kill weeds completely but leaves various weeds green and retards their growth over a long period of time, that is, a plant growth retardant. Upon actual weed growth control, on the other hand, an amount of the agent used differs with the place to be sprayed owing to the influence of wind or the like. A plant growth retardant is, consequently, required to exhibit plant growth retarding effects at a wide range of amount of it used. In other words, there is a requirement for the development of a plant growth retardant which does not destroy the root of weeds even if the amount of it used is a little larger than its standard amount and at the same time and which exhibits plant growth retarding effects even if the amount of it used is a little smaller than its standard amount.

There have been attempts to use the above-described nonselective herbicide at a reduced amount of it or to use the nonselective herbicide as a plant growth retardant after adding thereto an agent for suppressing its herbicidal activity (Japanese Examined Patent Publication No. Sho 56-6402, Japanese Unexamined Patent Publication No. Sho 59-101500, Weed Science, 39, 622–628(1991)). Such attempts are however accompanied with the drawbacks that the plant growth retarding effects are not exhibited at a wide range of amount of herbicide used, the plant growth retarding spectrum is narrow, the plant growth retarding effects do not continue long and the like and, therefore, have not yet reached a practical use. There is accordingly a demand for the development of a plant growth retardant which can overcome the above-described defects.

In addition, there have been various attempts to develop a herbicide which has a wide herbicidal spectrum, has high safety for circumstances and shows selectivity on crops (European Patent EP 431545 and the like), but it has not yet been practically utilized. There is accordingly a demand for the development of a herbicide having wide herbicidal spectrum and excellent selectivity on crops.

DISCLOSURE OF THE INVENTION

The present inventors have carried out an extensive investigation on a blending agent with a nonselective herbicide such as glyphosate for long years and have consequently found an agricultural chemical composition usable as a plant growth retardant or crop selective herbicide by incorporating the nonselective herbicide with a component composed of a phosphorus acid derivative and the like and optionally a component composed of a plant growth regulator, a bactericide and the like.

In the present invention, there are provided an agricultural chemical composition which comprises one or more than one first component having herbicidal activity selected from the below-described component group (a) consisting of nonselective phosphoric acid herbicides and one or more than one second component selected from the below-described component group (b) consisting of phosphorus acid derivatives and the like and optionally at least one third component selected from the below-described component group (c) consisting of maleic hydrazide and the like; and the use of said composition as a plant growth retardant and a crop selective herbicide;

said component group (a) consisting of:
  N-(phosphonomethyl)glycine or a salt thereof,
  N,N-bis(phosphonomethyl)glycine or a salt thereof,
  4-[hydroxy(methyl)phosphinoyl]-L-homoalanyl-L-alanyl-L-alanine or a salt thereof, and
  4-[hydroxy(methyl)phosphinoyl]-DL-homoalanine or a salt thereof;

said component group (b) consisting of:
  phosphorus acid derivatives each represented by the following formula (I):

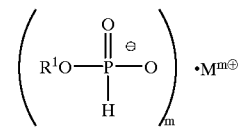

(I)

[wherein $R^1$ represents a $C_{1-8}$ alkyl group (said alkyl group may be substituted with 1 to 3 halogen atoms or 1 to 3 $C_{1-3}$ alkoxy groups), a phenyl group or a benzyl group; M represents a hydrogen atom, an ammonium group (said ammonium group may be substituted with 1 to 4 $C_{1-3}$ alkyl groups), a sodium atom, a potassium atom, a lithium atom, a magnesium atom, a calcium atom, a barium atom, a zinc atom, a manganese atom, a copper atom, an iron atom, a nickel atom or an aluminum atom; and m stands for an integer equivalent to the positive valency of M];

chitosan derivatives each represented by the following formula (II):

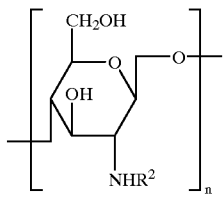

(II)

[wherein n stands for an integer not less than 1 and R² represents a hydrogen atom, a $C_{1-6}$ alkyl group or a $C_{1-11}$ acyl group.];

isopropyl phosphate salts selected from the group consisting of the magnesium salt, barium salt, aluminum salt, calcium salt and iron salt of isopropyl phosphate, organic acid metal salts selected from the group consisting of magnesium salts, barium salts, aluminum salts and calcium salts of at least one organic acid selected from the group consisting of lactic acid, propionic acid, formic acid, acetic acid, levulinic acid, benzoic acid, citric acid, alginic acid, L-(+)-ascorbic acid and salicylic acid {with the proviso that magnesium acetate and calcium acetate are excluded when the first component having herbicidal activity contains N-(phosphonomethyl)glycine or a salt thereof}, and organic metal salts selected from magnesium ethoxide and aluminum acetyl acetate; and inorganic metal salts selected from the group consisting of aluminum nitrate, calcium phosphinate, ammonium aluminum sulfate and potassium aluminum sulfate; and said component group (c) consisting of:

plant growth regulators, fungicides (inhibitors of ergosterol biosynthesis), mefluidide, atrazine, pyridate and clopyralid.

The N-(phosphonomethyl)glycine which may be a first component having herbicidal activity of the present invention is a nonselective herbicide commonly known as glyphosate.

The N,N-bis(phosphonomethyl)glycine which may be a first component having herbicidal activity of the present invention is a nonselective herbicide commonly known as glyphosine.

The 4-[hydroxy(methyl)phosphinoyl]-L-homoalanyl-L-alanyl-L-alanine which may be a first component having herbicidal activity of the present invention is a nonselective herbicide commonly known as bialaphos.

The 4-[hydroxy(methyl)phosphinoyl]-DL-homoalanine which may be a first component having herbicidal activity of the present invention is a nonselective herbicide commonly known as glufosinate.

The followings are structures of the first component having herbicidal activity of the present invention.

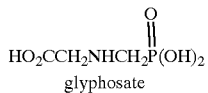
glyphosate

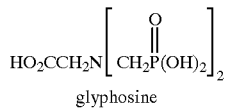
glyphosine

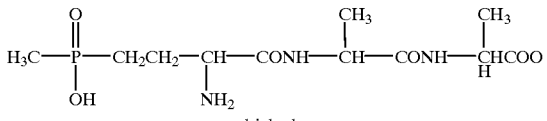
bialaphos

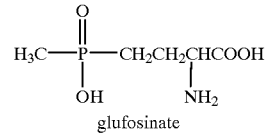
glufosinate

There is no particular limitation on the "salt thereof" in the first component having herbicidal activity provided that it is an organic or inorganic salt usable as an agricultural chemical. Examples of the inorganic base salt include alkali metal salts such as sodium salts, potassium salts and lithium salts, alkaline earth metal salts such as calcium salts and ammonium salts, while examples of the organic base salt include dimethylamine salts, triethylamine salts, isopropylamine salts, diisopropylamine salts, piperazine salts, pyrrolidine salts, piperidine salts, 2-phenylethylbenzylamine salts, benzylamine salts, ethanolamine salts, diethanolamine salts and triethylsulfonium salts. As the salt of N-(phosphonomethyl)glycine, the ammonium salt, isopropylamine salt, sodium salt or trimethylsulfonium salt is preferred, of which the isopropylamine salt or trimethylsulfonium salt is more preferred. As the salt of N,N-bis(phosphonomethyl)glycine, the sodium salt is preferred. As the salt of 4-[hydroxy(methyl)phosphinoyl]-L-homoalanyl-L-alanyl-L-alanine, the sodium salt is preferred. As the salt of 4-[hydroxy(methyl)phosphinoyl]-DL-homoalanine, the ammonium salt is preferred.

When used as a plant growth retardant, the first component having herbicidal activity of the present invention is preferably N-(phosphonomethyl)glycine or a salt thereof, or 4-[hydroxy(methyl)phosphinoyl]-DL-homoalanine or a salt thereof, of which the N-(phosphonomethyl)glycine or a salt thereof is more preferred. When used as a crop selective herbicide, 4-[hydroxy(methyl)phosphinoyl]-DL-homoalanine or a salt thereof is preferred.

In the phosphorus acid derivatives each represented by the above-described formula (I) which may serve as a second component of the present invention, examples of the "$C_{1-8}$ alkyl group" include chain or cyclic $C_{1-8}$ alkyl groups such as methyl, ethyl, propyl, isopropyl, butyl, isobutyl, s-butyl, t-butyl, pentyl, neopentyl, cyclopentyl, hexyl, cyclohexyl, heptyl, cycloheptyl and octyl, of which the $C_{1-4}$ alkyl groups such as methyl, ethyl, propyl, isopropyl, butyl, isobutyl, s-butyl and t-butyl groups are preferred and the ethyl group is more preferred.

In the phosphorus acid derivatives each represented by the above-described formula (I) which may serve as a second component of the present invention, examples of the "halogen atom" include, for example, fluorine, chlorine, bromine and iodine atoms, of which the chlorine atom is preferred.

In the phosphorus acid derivatives each represented by the above-described formula (I) which may serve as a second component of the present invention, examples of the "$C_{1-3}$ alkoxy group" include methoxy, ethoxy, propoxy and isopropoxy groups, of which the methoxy group is preferred.

In the phosphorus acid derivatives each represented by the above-described formula (I) which may serve as a second component of the present invention, examples of the "$C_{1-8}$ alkyl group substituted with 1 to 3 halogen atoms or 1 to 3 $C_{1-3}$ alkoxy groups" include the above-exemplified "$C_{1-8}$ alkyl group" substituted with 1 to 3 "halogen atom"s exemplified above or 1 to 3 "$C_{1-3}$ alkoxy group"s exemplified above such as chloromethyl, fluoromethyl, 2-chloroethyl, 1-chloroethyl, 2-fluoroethyl, 1-fluoroethyl, 2-bromoethyl, 2-iodoethyl, difluoromethyl, 2,2-difluoroethyl, 2,2,2-trichloroethyl, 2,2,2-trifluoroethyl, 3-chloropropyl, 3-fluoropropyl, 4-chlorobutyl, 5-chloropentyl, 6-chlorohexyl, 7-chloroheptyl, 8-chlorooctyl, 2-chlorocyclopentyl, 2-chlorocyclohexyl, methoxymethyl, ethoxymethyl, propoxymethyl, isopropoxymethyl, 2-methoxyethyl, 2-ethoxyethyl, 2-isopropoxyethyl, 3-methoxypropyl, 4-methoxybutyl, 5-methoxypentyl, 2-methoxycyclopentyl, 2-methoxycyclohexyl, 8-methoxyoctyl, 1,2-dimethoxyethyl and 1,2,3-trimethoxypropyl, of which the 2-chloroethyl, 2-fluoroethyl, 2-methoxyethyl or 2-methoxyethyl group is preferred.

In the phosphorus acid derivatives each represented by the above-described formula (I) which may serve as a second component of the present invention, examples of the "$C_{1-3}$ alkyl group" include methyl, ethyl, propyl and isopropyl groups, of which the ethyl group is preferred.

In the phosphorus acid derivatives each represented by the above-described formula (I) which may serve as a second component of the present invention, preferred as $R^1$ are the $C_{1-4}$ alkyl groups such as methyl, ethyl, propyl, isopropyl, butyl, isobutyl, s-butyl and t-butyl groups, of which the ethyl group is more preferred.

In the phosphorus acid derivatives each represented by the above-described formula (I) which may serve as a second component of the present invention, it is preferred that M represents magnesium and m stands for 2, M represents calcium and m stands for 2, M represents barium and m stands for 2, and M represents aluminum and m stands for 3, of which it is more preferred that M represents aluminum and m stands for 3.

In the chitosan derivatives each represented by the above-described formula (II) which may serve as a second component of the present invention, examples of the "$C_{1-6}$ alkyl group" include chain or cyclic $C_{1-6}$ alkyl groups such as methyl, ethyl, propyl, butyl, pentyl and hexyl groups, of which the methyl, ethyl or propyl group is preferred and the methyl or ethyl group is more preferred.

In the chitosan derivatives each represented by the above-described formula (II) which may serve as a second component of the present invention, examples of the "$C_{1-11}$ acyl group" include formyl, acetyl, propionyl, butyryl, acryloyl, methacryloyl, benzoyl and naphthoyl groups, of which the formyl, acetyl, butyryl or benzoyl group is preferred and the formyl or acetyl group is more preferred.

In the chitosan derivatives each represented by the above-described formula (II) which may serve as a second component of the present invention, n preferably stands for 1 to 10000, more preferably 1 to 1000 and most preferably 10 to 200.

In the chitosan derivatives each represented by the above-described formula (II) which may serve as a second component of the present invention, $R^2$ preferably represents a hydrogen atom or acetyl group.

In the chitosan derivatives each represented by the above-described formula (II) which may serve as a second component of the present invention, chitosan is preferred.

Another name of the "chitosan" as a second component of the present invention is β-1,4-poly-D-glucosamine which can be prepared by treating powdery chitin with a hot concentrated alkali. Examples of the commercially available products include chitosan (crab shell) of Aldrich Chemical Co., Ltd.; chitosan (crab shell) of Nacalai Tesque, Inc.; water soluble chitosans, Chitosan 10 (viscosity range: 5 to 20 cp), Chitosan 100 (viscosity range: 5 to 20 cp), Chitosan 100 (viscosity range: 50 to 150 cp), Chitosan 500 (viscosity range: 300 to 800 cp) and Chitosan 1000 (viscosity range: 800 to 1300 cp) of Wako Pure Chemical Industries, Ltd.; chitosans (molecular weight: up to 7000, up to 750000 and up to 2000000) of Furuka Fine Chemical Co., Ltd.; chitosan (deacetylation degree: 97%) of Katakura Chikkarin Co., Ltd.; and chitosans (deacetylation degree: 65, 68, 85, 93 and 96%) of Yaizu Suisankagaku Industry Co., Ltd. Any one of these chitosans is usable in the present invention.

The isopropyl phosphate salt as a second component of the present invention is a salt wherein a phosphate ester substituted with one or two isopropyl groups is bonded to a metal. Preferred examples include the magnesium salt, barium salt, aluminum salt and calcium salt, of which the aluminum salt is more preferred.

When the agricultural chemical composition of the present invention is employed as a plant growth retardant, the organic metal salt as a second component of the present invention is preferably an organic metal salt selected from the group consisting of magnesium salts, barium salts, aluminum salts and calcium salts of one organic acid selected from the group consisting of lactic acid, propionic acid, formic acid, acetic acid, levulinic acid, benzoic acid, citric acid, L-(+)-ascorbic acid and salicylic acid {with the proviso that magnesium acetate and calcium acetate are excluded when the first component having herbicidal activity contains N-(phosphonomethyl)glycine or a salt thereof}, and magnesium ethoxide, of which more preferred is the organic metal salt selected from the group consisting of magnesium salts, aluminum salts and calcium salts of one organic acid selected from the group consisting of lactic acid, propionic acid, formic acid, acetic acid, levulinic acid, benzoic acid, citric acid, L-(+)-ascorbic acid and salicylic acid {with the proviso that magnesium acetate and calcium acetate are excluded when the first component having herbicidal activity contains N-(phosphonomethyl)glycine or a salt thereof}, and magnesium ethoxide; still more preferred are magnesium lactate, aluminum lactate, calcium lactate, calcium propionate, aluminum acetate, calcium levulinate, calcium benzoate, magnesium citrate, calcium citrate or calcium salicylate; and most preferred are magnesium lactate, aluminum lactate, calcium lactate, calcium propionate, magnesium citrate or calcium citrate. When the agricultural chemical composition of the present invention is employed as a crop selective herbicide, on the other hand, preferred is an organic metal salt selected from the group consisting of magnesium salts, barium salts, aluminum salts and calcium salts of one organic acid selected from the group consisting of lactic acid, propionic acid, acetic acid, levulinic acid, benzoic acid, citric acid and alginic acid {with the proviso that magnesium acetate and calcium acetate are excluded when the first component having herbicidal activity contains N-(phosphonomethyl)glycine or a salt thereof}, and aluminum acetyl acetate; of which more preferred is the organic metal salt selected from the group consisting of magnesium salts, barium salts, aluminum salts and calcium salts of one organic acid selected from the group consisting of lactic acid, propionic acid, acetic acid, levulinic acid, benzoic acid, citric acid and alginic acid {with the proviso that calcium acetate is excluded when the first component having herbicidal activity contains N-(phosphonomethyl)glycine or a salt thereof}, and aluminum acetyl acetate; still more preferred are aluminum lactate, calcium lactate, calcium propionate, aluminum acetate, calcium acetate, calcium levulinate, calcium benzoate, calcium citrate or calcium alginate; and most preferred are aluminum lactate, aluminum acetate or calcium acetate.

The inorganic metal salt which may serve as a second component of the present invention is preferably aluminum nitrate, ammonium aluminum sulfate or potassium aluminum sulfate, of which ammonium aluminum sulfate or potassium aluminum sulfate is more preferred.

When the agricultural chemical composition of the present invention is used as a plant growth retardant, the second component of the present invention is preferably one or more than one compound selected from the group consisting of:

phosphorus acid derivatives each represented by the above-described formula (I) [wherein $R^1$ represents a $C_{1-4}$ alkyl group, M represents a magnesium atom, calcium atom, barium atom or aluminum atom and m stands for an integer equivalent to the positive valency of M];

chitosan derivatives each represented by the above-described formula (II) [wherein n stands for an integer of 1 or greater and $R^2$ represents a hydrogen atom or an acetyl group];

the aluminum salt of isopropyl phosphate;

organic metal salts selected from the group consisting of magnesium salts, aluminum salts and calcium salts of one organic acid selected from the group consisting of lactic acid, propionic acid, formic acid, acetic acid, levulinic acid, benzoic acid, citric acid, L-(+)-ascorbic acid and salicylic acid {with the proviso that magnesium acetate and calcium acetate are excluded when the first component having herbicidal activity contains N-(phosphonomethyl)glycine or a salt thereof}, and magnesium ethoxide; and inorganic metal salts selected from the group consisting of aluminum nitrate, ammonium aluminum sulfate and potassium aluminum sulfate, of which:

more preferred is one or more than one compound selected from the group consisting of:

phosphorus acid derivatives each represented by the above-described formula (I) [wherein $R^1$ represents an ethyl group, M represents an aluminum atom and m stands for 3];

chitosan;

organic metal salts selected from the group consisting of magnesium lactate, aluminum lactate, calcium lactate, calcium propionate, aluminum acetate, calcium levulinate, calcium benzoate, magnesium citrate, calcium citrate, calcium salicylate and magnesium ethoxide; and inorganic metal salts selected from the group consisting of aluminum nitrate, ammonium aluminum sulfate and potassium aluminum sulfate; and still more preferred is one or more than one compound selected from the group consisting of:

fosetyl aluminum salt;

organic metal salts selected from the group consisting of magnesium lactate, aluminum lactate, calcium lactate, calcium propionate, magnesium citrate and calcium citrate; and inorganic metal salts selected from the group consisting of ammonium aluminum sulfate and potassium aluminum sulfate.

When the agricultural chemical composition of the present invention is used as a crop selective herbicide, the second component is preferably one or more than one compound selected from the group consisting of:

phosphorus acid derivatives each represented by the above-described formula (I) [wherein $R^1$ represents a $C_{1-4}$ alkyl group, M represents a magnesium atom, calcium atom, barium atom, iron atom or aluminum atom and m stands for an integer equivalent to the positive valency of M];

chitosan derivatives each represented by the above-described formula (II) [wherein n stands for an integer of 1 or greater and $R^2$ represents a hydrogen atom or an acetyl group]; and organic acid metal salts selected from the group consisting of aluminum salts and calcium salts of one organic acid selected from the group consisting of lactic acid, propionic acid, acetic acid, levulinic acid, benzoic acid, citric acid and alginic acid {with the proviso that magnesium acetate and calcium acetate are excluded when the first component having herbicidal activity contains N-(phosphonomethyl)glycine or a salt thereof} and aluminum acetyl acetate, of which:

more preferred is one or more than one compound selected from the group consisting of:

phosphorus acid derivatives each represented by the above-described formula (I) [wherein $R^1$ represents an ethyl group, M represents an aluminum atom and m stands for 3];

chitosan; and organic metal salts selected from the group consisting of aluminum lactate, calcium lactate, calcium propionate, aluminum acetate, calcium acetate, calcium levulinate, calcium benzoate, calcium citrate, calcium alginate and aluminum acetyl acetate; and still more preferred is one or more than one compound selected from the group consisting of:

fosetyl aluminum salt and organic metal salts selected from the group consisting of aluminum lactate, aluminum acetate, calcium acetate and aluminum acetylacetate.

Examples of the plant growth regulator, which may be a third component of the present invention, include:

maleic hydrazide or a salt thereof (there is no particular limitation on the nature of the "salt thereof" provided that it can be usually used for an agricultural chemical and examples include sodium salt, potassium salt, diethanolamine salt and choline salt, of which the potassium salt or choline salt is preferred), uniconazole ((E)-(RS)-1-(4-chlorophenyl)-4,4-dimethyl-2-(1H-1,2,4-triazol-1-yl)-1-penten-3-ol), flurprimidol ((RS)-2-methyl-1-pyrimidin-5-yl-1-(4-trifluoromethoxyphenyl)propan-1-ol), inabenfide (4'-chloro-2'-(α-hydroxybenzyl)isonicotinanilide), chlormequat chloride (2-chloroethyltrimethylammonium chloride), dikegulac (2,3:4,6-di-O-isopropylidene-α-L-xylo-2-hexulofuranosonic acid), ancymidol (α-cyclopropyl-4-methoxy-α-(pyrimidin-5-yl)benzylalcohol), abscisic acid, paclobutrazol ((2RS,3RS)-1-(4-chlorophenyl)-4,4-dimethyl-2-(1H-1,2,4-triazol-1-yl)pentan-3-ol), trinexapac-ethyl (ethyl 4-cyclopropyl(hydroxy)methylene-3,5-dioxocyclohexanecarboxylate), prohexadione-calcium (calcium 3,5-dioxo-4-propionylcyclohexanecarboxylate) and choline chloride (2-hydroxyethyltrimethylammonium chloride). They are all known compounds. For the use for a plant growth retardant, maleic hydrazide or a salt thereof, flurprimidol, abscisic acid, paclobutrazol, trinexapac-ethyl or prohexadione-calcium is preferred, of which the maleic hydrazide or salt thereof is more preferred. For the use for a crop selective herbicide, uniconazole or inabenfide is preferred.

Examples of the fungicide (biosynthesis inhibitor of ergosterol) which may be a third component of the present invention include:

triadimefon (1-(4-chlorophenoxy)-3,3-dimethyl-1-(1H-1,2,4-triazol-1-yl)butan-2-one), triflumizole ((E)-4-chloro-α,α,α-trifluoro-N-(1-imidazol-1-yl-2-propoxyethylidene)-o-toluidine), pyrifenox (2',4'-dichloro-2-(3-pyridyl)acetophenone (EZ)-O-methyloxime), propiconazole ((±)-1-[2-(2,4-dichlorophenyl)-4-propyl-1,3-dioxolan-2-ylmethyl]-1H-1,2,4-triazole), and 2-(4-fluorophenyl)-1-(1H-1,2,4-triazol-1-yl)-3-trimethylsilyl-2-propanol (Japanese Patent Application Kokai No. Hei 5-22060). They are all known compounds. For the use for a plant growth retardant, triadimefon, triflumizole or 2-(4-fluorophenyl)-1-(1H-1,2,4-triazol-1-yl)-3-trimethylsilyl-2-propanol is preferred, while for the use for a crop selective herbicide, 2-(4-fluorophenyl)-1-(1H-1,2,4-triazol-1-yl)-3-trimethylsilyl-2-propanol is preferred.

Examples of other compounds which may be the third component in the present invention include:

mefluidide (5'-(1,1,1-trifluoromethanesulfonamido)aceto-2',4'-xylidide), atrazine (6-chloro-N-ethyl-N'-(1-methylethyl)-1,3,5-triazine-2,4-diamine), pyridate (O-(6-chloro-3-phenylpyridazin-4-yl)-S-octylthiocarbonate) and clopyralid (3,6-dichloropyridine-2-carboxylic acid). They are all known compounds. For the use for a plant growth retardant, mefluidide is preferred, while for the use for a crop selective herbicide, atrazine, pyridate or clopyralid is preferred, of which atrazine or pyridate is more preferred.

Following are the structures of the compounds usable as the third component of the present invention.

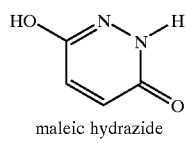
maleic hydrazide

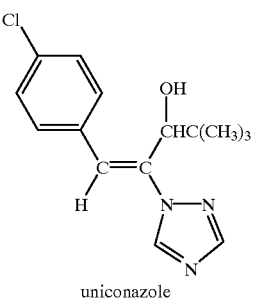
uniconazole

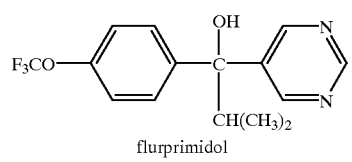
flurprimidol

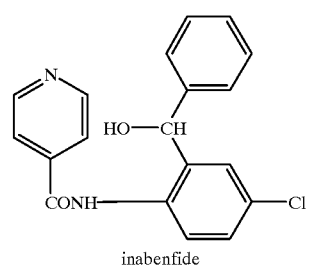
inabenfide

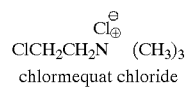
chlormequat chloride

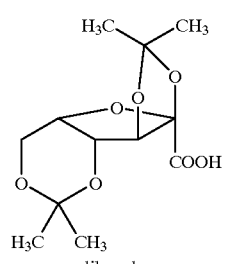
dikegulac

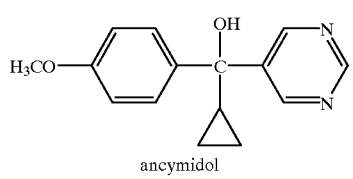
ancymidol

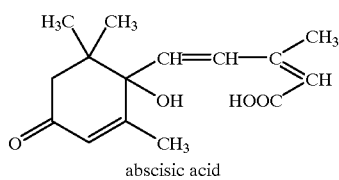
abscisic acid

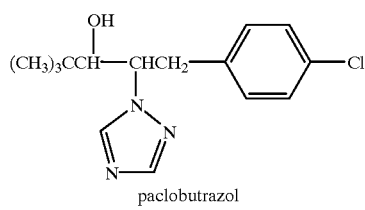
paclobutrazol

-continued

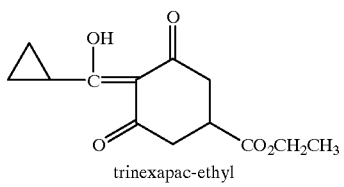
trinexapac-ethyl

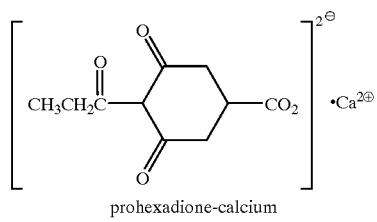
prohexadione-calcium

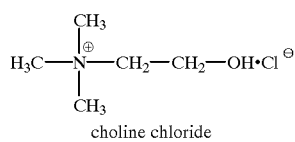
choline chloride

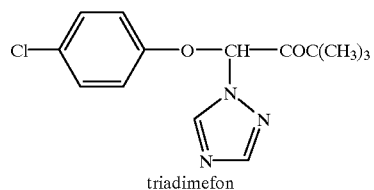
triadimefon

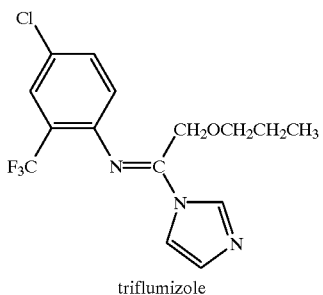
triflumizole

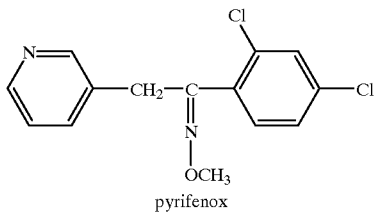
pyrifenox

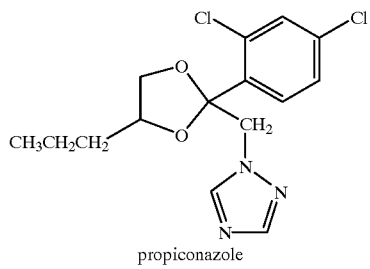
propiconazole

-continued

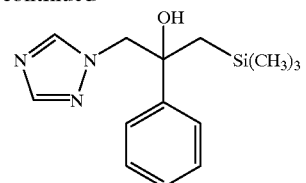
Japanese Unexamined Patent
Publication No. Hei 5-22060

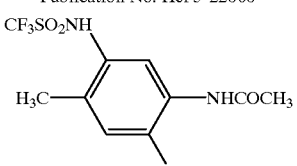
mefluidide

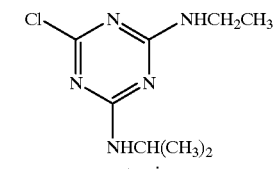
atrazine

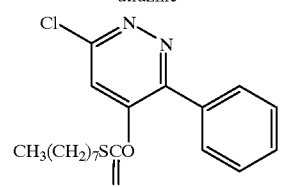
pyridate

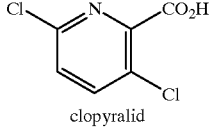
clopyralid

For the use for a plant growth retardant, the third component of the present invention is preferably one or more than one compound selected from the group consisting of plant growth regulators, fungicides (inhibitors of ergosterol biosynthesis) and mefluidide, of which:

more preferred is one or more than one compound selected from plant growth regulators;

still more preferred is one or more than one compound selected from the group consisting of maleic hydrazide and salts thereof, flurprimidol, abscisic acid, paclobutrazol, trinexapac-ethyl and prohexadione-calcium; and most preferred is one or more than one compound selected from the group consisting of maleic hydrazide and salts thereof.

For the use for a crop selective herbicide, the third component of the present invention is preferably one or more than one compound selected from the group consisting of atrazine, pyridate and clopyralid, of which more preferred is one or more than one compound selected from the group consisting of atrazine and pyridate.

In one aspect of the present invention, there is thus provided (1) an agricultural chemical composition which comprises one or more than one first component having herbicidal activity selected from the below-described component group (a) and one or more than one second component selected from the below-described component group (b) and optionally one or more than one third component selected from the below-described component group (c);

said component group (a) consisting of:
N-(phosphonomethyl)glycine or a salt thereof,
N,N-bis(phosphonomethyl)glycine or a salt thereof,
4-[hydroxy(methyl)phosphinoyl]-L-homoalanyl-L-alanyl-L-alanine or a salt thereof, and
4-[hydroxy(methyl)phosphinoyl]-DL-homoalanine or a salt thereof, said component group (b) consisting of:
phosphorus acid derivatives each represented by the following formula (I):

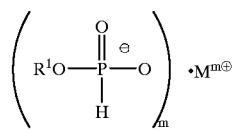

[wherein $R^1$ represents a $C_{1-8}$ alkyl group (said alkyl group may be substituted with 1 to 3 halogen atoms or 1 to 3 $C_{1-3}$ alkoxy groups), a phenyl group or a benzyl group; M represents a hydrogen atom, an ammonium group (said ammonium group may be substituted with 1 to 4 $C_{1-3}$ alkyl groups), a sodium atom, a potassium atom, a lithium atom, a magnesium atom, a calcium atom, a barium atom, a zinc atom, a manganese atom, a copper atom, an iron atom, a nickel atom or an aluminum atom; and m stands for an integer equivalent to the positive valency of M];

chitosan derivatives each represented by the following formula (II):

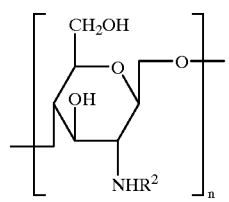

[wherein n stands for an integer of 1 or greater and $R^2$ represents a hydrogen atom, a $C_{1-6}$ alkyl group or a $C_{1-11}$ acyl group];

isopropyl phosphate salts selected from the group consisting of the magnesium salt, barium salt, aluminum salt, calcium salt and iron salt of isopropyl phosphate;

organic metal salts selected from the group consisting of magnesium salts, barium salts, aluminum salts and calcium salts of one organic acid selected from the group consisting of lactic acid, propionic acid, formic acid, acetic acid, levulinic acid, benzoic acid, citric acid, alginic acid, L-(+)-ascorbic acid and salicylic acid {with the proviso that magnesium acetate and calcium acetate are excluded when the first component having herbicidal activity contains N-(phosphonomethyl)glycine or a salt thereof), magnesium ethoxide and aluminum acetyl acetate; and inorganic metal salts selected from the group consisting of aluminum nitrate, calcium phosphinate, ammonium aluminum sulfate and potassium aluminum sulfate; and said component group (c) consisting of:
plant growth regulators, fungicides (inhibitors of ergosterol biosynthesis), mefluidide, atrazine, pyridate and clopyralid.

In a preferred aspect of the present invention, there are also provided:

(2) an agricultural chemical composition as described in (1), wherein the first component having herbicidal activity is one or more than one compound selected from the group consisting of N-(phosphonomethyl)glycine or a salt thereof and 4-[hydroxy(methyl)phosphinoyl]-DL-homoalanine or a salt thereof, (3) an agricultural chemical composition as described in (1), wherein the first component having herbicidal activity is N-(phosphonomethyl)glycine or a salt thereof, (4) an agricultural chemical composition as described in any one of (1) to (3), wherein the second component is one or more than one compound selected from the below-described component group (b1), said component group (b1) consisting of:
phosphorus acid derivatives each represented by the following formula (I):

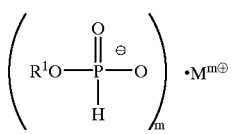

[wherein $R^1$ represents a $C_{1-4}$ alkyl group, M represents a magnesium atom, a calcium atom, a barium atom or an aluminum atom and m stands for an integer equivalent to the positive valency of M];

chitosan derivatives each represented by the following formula (II):

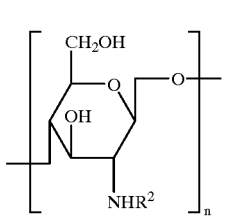

[wherein n stands for an integer of 1 or greater and $R^2$ represents a hydrogen atom or an acetyl group];

aluminum salt of isopropyl phosphate;

organic metal salts selected from the group consisting of magnesium salts, aluminum salts and calcium salts of one organic acid selected from the group consisting of lactic acid, propionic acid, formic acid, acetic acid, levulinic acid, benzoic acid, citric acid, L-(+)-ascorbic acid and salicylic acid {with the proviso that magnesium acetate and calcium acetate are excluded when the first component having herbicidal activity contains N-(phosphonomethyl)glycine or a salt thereof}, and magnesium ethoxide; and inorganic metal salts selected from the group consisting of aluminum nitrate, ammonium aluminum sulfate and potassium aluminum sulfate, (5) an agricultural chemical composition as described in any one of (1) to (3), wherein the second component is one or more than one compound selected from the below-described component group (b2), said component group (b2) consisting of:

phosphorus acid derivatives each represented by the following formula (I):

$$\left( R^1O-\underset{H}{\overset{\overset{O}{\|}}{P}}-O^{\ominus} \right)_m \cdot M^{m\oplus} \quad (I)$$

[wherein $R^1$ represents an ethyl group, M represents an aluminum atom and m stands for 3];

chitosan;

organic metal salts selected from the group consisting of magnesium lactate, aluminum lactate, calcium lactate, calcium propionate, aluminum acetate, calcium levulinate, calcium benzoate, magnesium citrate, calcium citrate, calcium salicylate and magnesium ethoxide; and inorganic metal salts selected from the group consisting of aluminum nitrate, ammonium aluminum sulfate and potassium aluminum sulfate, (6) an agricultural chemical composition as described in any one of (1) to (3), wherein the second component is one or more than one compound selected from the below-described component group (b3), said component group (b3) consisting of:

fosetyl aluminum salt;

organic metal salts selected from the group consisting of magnesium lactate, aluminum lactate, calcium lactate, calcium propionate, magnesium citrate and calcium citrate; and inorganic metal salts selected from the group consisting of ammonium aluminum sulfate and potassium aluminum sulfate, (7) an agricultural chemical composition as described in any one of (1) to (6), wherein the third component is one or more than one compound selected from the below-described component group (c1), said component group (c1) consisting of plant growth regulators, fungicides (inhibitors of ergosterol biosynthesis) and mefluidide, (8) an agricultural chemical composition as described in any one of (1) to (6), wherein the third component is one or more than one compound selected from plant growth regulators, (9) an agricultural chemical composition as described in any one of (1) to (6), wherein the third component is one or more than one compound selected from the below-described component group (c2), said component group (c2) consisting of maleic hydrazide and salts thereof, flurprimidol, abscisic acid, paclobutrazol, trinexapac-ethyl and prohexadione-calcium,

(10) an agricultural chemical composition as described in any one of (1) to (6), wherein the third component is one or more than one compound selected from the below-described component group (c3), said component group (c3) consisting of maleic hydrazide and salts thereof,

(11) a plant growth retardant comprising the agricultural chemical composition as described in any one of (1) to (10),

(12) a method of using an agricultural chemical composition as described in any one of (1) to (10) as a plant growth retardant,

(13) an agricultural chemical composition as described in (1), wherein the first component having herbicidal activity is one or more than one compound selected from the group consisting of 4-[hydroxy(methyl)phosphinoyl]-DL-homoalanine and salts thereof,

(14) an agricultural chemical composition as described in (1) or (13), wherein the second component is one or more than one compound selected from the below-described component group (b4), said component group (b4) consisting of:

phosphorus acid derivatives each represented by the above-described formula (I):

$$\left( R^1O-\underset{H}{\overset{\overset{O}{\|}}{P}}-O^{\ominus} \right)_m \cdot M^{m\oplus} \quad (I)$$

[wherein $R^1$ represents a $C_{1-4}$ alkyl group, M represents a magnesium atom, a calcium atom, a barium atom or an aluminum atom and m stands for an integer equivalent to the positive valency of M];

chitosan derivatives each represented by the following formula (II):

$$\left[ \begin{array}{c} CH_2OH \\ \text{(structure with OH and } NHR^2\text{)} \end{array} \right]_n \quad (II)$$

[wherein n stands for an integer of 1 or greater and $R^2$ represents a hydrogen atom or an acetyl group]; and organic metal salts selected from the group consisting of aluminum salts and calcium salts of one organic acid selected from the group consisting of lactic acid, propionic acid, acetic acid, levulinic acid, benzoic acid, citric acid and alginic acid {with the proviso that magnesium acetate and calcium acetate are excluded when the first component having herbicidal activity contains N-(phosphonomethyl)glycine or a salt thereof}, and aluminum acetylacetate,

(15) an agricultural chemical composition as described in (1) or (13), wherein the second component is one or more than one compound selected from the below-described component group (b5), said component group (b5) consisting of:

a phosphorus acid derivative represented by the following formula (I):

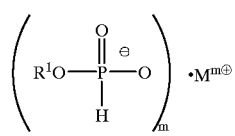

(I)

[wherein R¹ represents an ethyl group, M represents an aluminum atom and m stands for 3];
chitosan; and
organic metal salts selected from the group consisting of aluminum lactate, calcium lactate, calcium propionate, aluminum acetate, calcium acetate, calcium levulinate, calcium benzoate, calcium citrate, calcium alginate and aluminum acetylacetate,

(16) an agricultural chemical composition as described in (1) or (13), wherein the second component is one or more than one compound selected from the below-described component group (b6), said component group (b6) consisting of:
fosetyl aluminum salt;
organic metal salts selected from the group consisting of aluminum lactate, aluminum acetate, calcium acetate and aluminum acetylacetate,

(17) an agricultural chemical composition as described in (1) or any one of from (13) to (16), wherein the third component is one or more than one compound selected from the below-described component group (c4), said component group (c4) consisting of:
atrazine, pyridate and clopyralid,

(18) an agricultural chemical composition as described in (1) or any one of from (13) to (16), wherein the third component is one or more than one compound selected from the below-described component group (c5), said component group (c5) consisting of atrazine and pyridate,

(19) a crop selective herbicide comprising an agricultural chemical composition as described in (1) or any one of from (13) to (18), and

(20) a method of using an agricultural chemical composition as described in (1) or any one of from (13) to (18) as a crop selective herbicide.

The phosphorus acid derivative represented by the formula (1), which is the second component of the present invention, can be prepared in accordance with the preparation process as described in Japanese Patent Application Kokai No. Sho 50-94137.

In the agricultural chemical composition of the present invention, when the second component is the phosphorus acid derivative, isopropylphosphate salt, organic metal salt or inorganic metal salt, it is usually added in an amount of 0.001 to 100 parts by weight, preferably 0.01 to 20 parts by weight, more preferably 0.5 to 20 parts by weight relative to 1 part by weight of the first component having herbicidal activity. When the second component is a chitosan derivative, it is usually added in an amount of 0.01 to 300 parts by weight, preferably 0.1 to 200 parts by weight, more preferably 1 to 100 parts by weight.

In the agricultural chemical composition of the present invention, the third component is usually added in an amount of 0.1 to 500 parts by weight, preferably 1 to 50 parts by weight relative to 1 part by weight of the first component having herbicidal activity.

The composition according to the present invention is sprayed mainly to the stem and leaf parts of a plant. It is possible to spray the technical product of each component itself or to spray the components after mixing with a carrier and, if necessary, other adjuvants, thereby formulating into an ordinarily employed form as an agricultural chemical composition, for example, dust, coarse dust, micro granules, granules, wettable powder, emulsifiable concentrate, liquid preparation, suspension concentrate, water degradable granules or oil suspension.

As a means for carrying out the method of the present invention, it is possible to treat, before or after spraying a nonselective phosphorus acid herbicide which is a first component having herbicidal activity to a plant, the plant with the other components successively, as well as to carry out simultaneous treatment with a premix in which each of the above-described components has been mixed in advance or with the above-described components tank-mixed at the application site.

Suitable examples of a solid carrier to be used for the preparation of the agricultural chemical composition of the present invention include inorganic substances such as kaolinite, pyrophyllite, montmorillonite, attapulgite, pyrophyllite, talc, mica, pumice, vermiculite, gypsum, calcium carbonate, dolomite, diatomaceous earth, magnesium lime, apatite, zeolite, silicic anhydride and synthetic calcium silicate; vegetable organic substances such as soybean flour, tobacco flour, walnut flour, wheat flour, wood flour, starch and crystalline cellulose; synthetic or natural resins such as coumarone resin, petroleum resin, alkyd resin, ketone resin, ester gum, copal gum and dammar gum; synthetic high molecules such as polyvinyl chloride and polyalkylene glycol; waxes such as carnauba wax and bees wax; and urea.

Suitable examples of the liquid carrier include paraffin or naphthene hydrocarbons such as kerosine, mineral oil, spindle oil and white oil; aromatic hydrocarbons such as benzene, toluene, xylene, ethylbenzene, cumene and methylnaphthalene; chlorinated hydrocarbons such as carbon tetrachloride, chloroform, trichloroethylene, monochlorobenzene and o-chlorotoluene; ethers such as dioxane and tetrahydrofuran; ketones such as acetone, methyl ethyl ketone, diisobutyl ketone, cyclohexanone, acetophenone and isophorone; esters such as ethyl acetate, amyl acetate, ethylene glycol acetate, dibutyl maleate and diethyl succinate; alcohols such as methanol, hexanol, ethylene glycol, diethylene glycol, cyclohexanol and benzine alcohol; ether alcohols such as ethylene glycol ethyl ether, ethylene glycol phenyl ether, diethylene glycol ethyl ether and diethylene glycol butyl ether; polar solvents such as dimethylformamide and dimethylsulfoxide; and water.

As a surfactant to be used for the purpose of emulsification, dispersion, wetting, spreading, integration, disintegration control, stabilization of active ingredients, improvement of fluidity or rust inhibition, any one of nonionic, anionic, cationic and amphoteric ones may be used, of which the nonionic or anionic one is usually employed. Suitable examples of the nonionic surfactant include an addition polymerization product of higher alcohols, such as lauryl alcohol, stearyl alcohol and oleyl alcohol, with ethylene oxide; an addition polymerization product of alkyl phenols, such as isooctylphenol and nonylphenol, with ethylene oxide; an addition polymerization product of alkyl naphthols, such as butylnaphthol and octylnaphthol, with ethylene oxide; an addition polymerization product of higher fatty acids, such as palmitic acid, stearic acid and oleic acid, with ethylene oxide; mixtures of mono-, di- and tri-phosphoric acid esters of the above-exemplified nonionic surfactant or sulfate esters and salts thereof; an addition polymerization product of amines, such as dodecyl amine or stearic acid amide, with ethylene oxide; and an addition polymerization product of higher fatty acid esters of a polyhydric alcohol, such as sorbitan and these esters with ethylene oxide and propylene oxide. Suitable examples of the anionic surfactant include alkylsulfate ester salts such as sodium laurylsulfate and oleyl alcohol sulfuric acid ester amine salt; and arylsulfonic acids such as sulfosuccinic acid dioctyl ester sodium, sodium isopropylnaphthalene sulfonate, sodium methylenebisnaphthalenesulfonate, sodium ligninsulfonate and sodium dodecylbenzenesulfonate.

In order to improve the properties of the formulation and enhance the biological activity, it is also possible to add to the agricultural chemical composition of the present invention a highpolymer compound such as casein, gelatin, albumin, glue, sodium alginate, carboxymethyl cellulose, methyl cellulose, hydroxyethyl cellulose or polyvinyl alcohol or other adjuvants.

In consideration of the type of formulation and practical use, the above-described carriers and various adjuvants may be used singly or in combination at an appropriate time according to the purpose.

The powder usually contains, for example, 1 to 25 parts by weight of the active ingredient and the remaining portion is a solid carrier.

The wettable powder contains, for example, 25 to 90 parts by weight of the active ingredient and the remaining portion comprises a solid carrier and dispersible humectant. A protective colloid, thixotropic agent, antifoaming agent and the like may be added if necessary.

The granules contain, for example, 1 to 35 parts by weight of the active ingredient and the most of the remaining portion is a solid carrier. The active ingredient is mixed uniformly with the solid carrier or is adhered or adsorbed to the surface of the solid carrier uniformly. The granules have a particle size of about 0.2 to 1.5 mm.

The emulsifiable concentrate contains, for example, 5 to 30 parts by weight of the active ingredient and 5 to 20 parts by weight of an emulsifying agent. The remaining portion is a liquid carrier. If necessary, a rust preventive may be added.

The agricultural chemical composition of the present invention to be sprayed in various types of formulation is used so that the first component having herbicidal activity might be sprayed in an amount of 0.1 to 10 kg, preferably 0.3 to 5 kg/ha and the second component might be sprayed in an amount of 0.1 to 500 kg/ha, preferably 0.5 to 50 kg/ha. When the agricultural chemical composition of the present invention contains the third component, it is used so that the third component might be sprayed in an amount of 0.1 to 500 kg/ha, preferably 0.5 to 50 kg/ha.

There is no particular limitation on the time using the agricultural chemical composition of the present invention as a crop selective herbicide. It is preferred that with reference to corn as a crop, the agricultural chemical composition is used when the height of the corn is 20 cm or greater, while with reference to cotton as the crop, the composition is used when the height of the cotton is 5 cm or greater.

A specific description will next be made on the conditions under which the agricultural chemical composition of the present invention exhibits crop selectivity. For example, when the height of the corn grown under the optimum temperature is 15 cm or greater, a composition comprising glufosinate ammonium as the first component having herbicidal activity and fosetyl aluminum salt or chitosan as the second component at a ratio of 1:1 to 10 is sprayed to weeds so that the amount of the first component might be 0.1 to 0.4 kg/ha. Then, the composition shows selective activity on corn and broadleaf weeds such as prickly sida, velvetleaf, wild mustard and morningglory can be controlled. When the composition further comprises as the third component atrazine or pyridate and the ratio of the first herbicidal component to the third component is 1:5 to 20, gramineous weeds such as annual bluegrass, Johnsongrass, Italian ryegrass and barnyardgrass can also be controlled. For example, when the height of the cotton grown under the optimum temperature is 5 cm or greater, a composition comprising glyphosate isopropylamine salt as the first component having herbicidal activity and fosetyl aluminum salt as the second component at a ratio of 1:1.5 to 5 or chitosan as the second component at a ratio of 1:5 to 20 is sprayed to weeds so that the amount of the first component might be 0.3 to 1 kg/ha. Then, the composition shows selective activity on cotton and gramineous weeds such as green foxtail, barnyardgrass and Johnsongrass and broadleaf weeds such as wild mustard can be controlled.

The present invention will hereinafter be described in further detail with reference to examples and tests. But the examples and the activity tests are not to be construed as limiting the scope of the invention in any way.

EXAMPLE 1

Wettable Powder

A uniform wettable powder was obtained by mixing and pulverizing 2 parts by weight of fosetyl aluminum salt, 1 part by weight of glyphosate isopropylamine salt, 86 parts by weight of clay, 3 parts by weight of white carbon, 5 parts by weight of sodium ligninsulfonate and 3 parts by weight of sodium alkylnaphthalenesulfonate.

EXAMPLE 2

Wettable Powder

A uniform wettable powder was obtained by mixing and pulverizing 2 parts by weight of fosetyl aluminum salt, 1 part by weight of glyphosate isopropylamine salt, 3 parts by weight of maleic hydrazide choline salt, 83 parts by weight of clay, 3 parts by weight of white carbon, 5 parts by weight of sodium ligninsulfonate and 3 parts by weight of alkyl naphthalenesulfonate.

EXAMPLE 3

Liquid Preparation

A liquid preparation was obtained by mixing 3 parts by weight of fosetyl aluminum salt, 1 part by weight of glufosinate ammonium and 96 parts by weight of water.

EXAMPLE 4

Liquid Preparation

A liquid preparation was obtained by mixing 2 parts by weight of fosetyl aluminum salt, 1 part by weight of glyphosate isopropylammonium, 3 parts by weight of maleic hydrazide choline salt and 94 parts by weight of water.

EXAMPLE 5

Liquid Preparation

A liquid preparation was obtained by mixing 2 parts by weight of calcium propionate, 1 part by weight of glyphosate isopropylamine salt and 97 parts by weight of water.

EXAMPLE 6

Liquid Preparation

A liquid preparation is obtained by mixing 6 parts by weight of calcium propionate, 1 part by weight of glyphosate isopropylamine salt, 6 parts by weight of maleic hydrazide and 87 parts by weight of water.

EXAMPLE 7

Granules

Granules are obtained by mixing 2 parts by weight of fosetyl aluminum salt, 1 part by weight of glyphosate isopropylamine salt, 30 parts by weight of bentonite, 2 parts by weight of sodium dodecylbenzenesulfonate and 3 parts by weight of sodium ligninsulfonate, further adding 62 parts of water, kneading the resulting mixture in a kneader, granulating the kneaded mass in a granulator, and then drying.

EXAMPLE 8

Wettable Powder

A uniform wettable powder is obtained by mixing and pulverizing 20 parts by weight of chitosan (water soluble chitosan, product of Wako Pure Chemicals Inc), 1 part by weight of glyphosate isopropylamine salt, 68 parts by weight of clay, 3 parts by weight of white carbon, 5 parts by weight of sodium ligninsulfonate and 3 parts by weight of sodium alkylnaphthalenesulfonate.

EXAMPLE 9

Liquid Preparation

A liquid preparation was obtained by mixing 20 parts by weight of chitosan (water soluble chitosan, product of Wako Pure Chemicals, Inc.), 1 part by weight of glyphosate isopropylamine salt and 79 parts by weight of water.

EXAMPLE 10

Granules

Granules are obtained by mixing 20 parts by weight of chitosan (water soluble chitosan, product of Wako Pure Chemicals, Inc.), 1 part by weight of glyphosate isopropylamine salt, 30 parts by weight of bentonite, 2 parts by weight of sodium dodecylbenzenesulfonate and 3 parts by weight of sodium ligninsulfonate, further adding 44 parts of water, kneading the resulting mixture in a kneader, granulating the kneaded mass in a granulator and then drying.

EXAMPLE 11

Wettable Powder

A uniform wettable powder is obtained by mixing and granulating 10 parts by weight of chitosan (water soluble chitosan, product of Wako Pure Chemicals, Inc.), 1 part by weight of glufosinate ammonium, 78 parts by weight of clay, 3 parts by weight of white carbon, 5 parts by weight of sodium ligninsulfonate and 3 parts by weight of sodium alkylnaphthalenesulfonate.

EXAMPLE 12

Liquid Preparation

A liquid preparation was obtained by mixing 10 parts by weight of chitosan (water soluble chitosan, product of Wako Pure Chemicals, Inc.), 1 part by weight of glufosinate ammonium and 89 parts by weight of water.

EXAMPLE 13

Granules

Granules are obtained by mixing 10 parts by weight of chitosan (water soluble chitosan, product of Wako Pure Chemicals, Inc.), 1 part by weight of bialaphos sodium salt, 30 parts by weight of bentonite, 2 parts by weight of sodium dodecylbenzenesulfonate and 3 parts by weight of ligninsulfonate, further adding 54 parts of water, kneading the resulting mixture in a kneader, granulating the kneaded mass in a granulator and then drying.

EXAMPLE 14

Liquid Preparation

A liquid preparation was obtained by mixing 6 parts by weight of calcium lactate, 1 part by weight of glufosinate ammonium and 93 parts by weight of water.

EXAMPLE 15

Wettable Powder

A uniform wettable powder was obtained by mixing and pulverizing 6 parts by weight of fosetyl aluminum salt, 1 part by weight of glufosinate ammonium, 84 parts by weight of clay, 3 parts by weight of white carbon, 5 parts by weight of sodium ligninsulfonate and 3 parts by weight of sodium alkylnaphthalenesulfonate.

EXAMPLE 16

Wettable Powder

A uniform wettable powder was obtained by mixing and pulverizing 10 parts by weight of fosetyl aluminum salt, 1 part by weight of glufosinate ammonium, 5 parts by weight of atrazine, 73 parts by weight of clay, 3 parts by weight of white carbon, 5 parts by weight of sodium ligninsulfonate and 3 parts by weight of sodium alkylnaphthalenesulfonate.

EXAMPLE 17

Wettable Powder

A uniform wettable powder is obtained by mixing and pulverizing 10 parts by weight of chitosan (water soluble chitosan, product of Wako Pure Chemicals, Inc.), 1 part by weight of glufosinate ammonium, 5 parts by weight of atrazine, 73 parts by weight of clay, 3 parts by weight of white carbon, 5 parts by weight of sodium ligninsulfonate and 3 parts by weight of sodium alkylnaphthalenesulfonate.

EXAMPLE 18

Wettable Powder

A uniform wettable powder was obtained by mixing and pulverizing 1 part by weight of chitosan (water soluble chitosan, product of Wako Pure Chemicals, Inc.), 1 part by weight of glufosinate ammonium, 10 parts by weight of atrazine, 77 parts by weight of clay, 3 parts by weight of white carbon, 5 parts by weight of sodium ligninsulfonate and 3 parts by weight of sodium alkylnaphthalenesulfonate.

(Test 1)

Plant Growth Retarding Effects by Glyphosate+Metal Salt

In a 5×150 cm$^3$ plastic pot filled with Kureha horticultural soil, seeds of barnyardgrass, green foxtail, Johnsongrass, Italian ryegrass, annual bluegrass and wild mustard were sowed and grown for 14 days in a greenhouse. Wettable powders or liquid preparation having the below-described metal salts incorporated therein were prepared respectively in accordance with Example 1 or Example 5, followed by dilution with water, whereby spray solutions were prepared. The spray solutions were sprayed to each plant. Upon preparation, the spray solutions were each adjusted so that the ion equivalent of the metal salt (=mole concentration of the metal ion in the spray solution×positive valency of the metal) might be 8.4 or 16.8 mM (1.2 or 2.4 mM in the case of barium salt) and the concentration of the glyphosate isopropylamine salt might be 1000 ppm. The sprayed volume was set at 1000 liters/ha. For comparison, tests were made using a composition containing a single preparation of glyphosate isopropylamine salt free from a metal salt and aluminum sulfate or calcium carbonate as a metal salt. After 14 days from the spraying, the degree of deaths of the plant and the height of the living plant were observed and the plant growth retarding effects of the spray solution were determined. The results are shown in Table 2. The plant growth retarding effects are expressed by a numeral or letter of the alphabet and the numeral or letter of the alphabet indicates the height suppressing rate shown in Table 1. In Table 2, b, f, J, I, a and w represent barnyardgrass, green foxtail, Johnsongrass, Italian ryegrass, annual bluegrass and wild mustard, respectively and—represents that no test was made.

TABLE 1

| Plant growth retarding effects | Plant height suppressing rate (%) |
| --- | --- |
| D | 100 (complete death) |
| 5 | 90–99 |
| 4 | 70–89 |
| 3 | 50–69 |
| 2 | 30–49 |
| 1 | 10–29 |
| 0 | 0–9 |

TABLE 2

Plant growth retarding effects by 1000 ppm of glyphosate + metal salt

| Metal salt to be mixed with glyphosate (concentration in terms of metal ion: ppm) | | Ion equiva- lent (mM) | Plant growth retarding effects | | | | | |
| --- | --- | --- | --- | --- | --- | --- | --- | --- |
| | | | b | f | J | I | a | w |
| None (single glyphosate preparation) | | | D | D | D | D | D | D |
| Aluminum nitrate | (76) | 8.4 | 2 | 3 | 2 | 3 | 2 | 2 |
| | (152) | 16.8 | 3 | 3 | 2 | 3 | 2 | 3 |
| Aluminum ammonium sulfate | (76) | 8.4 | 4 | 4 | 4 | 4 | 3 | 3 |
| | (152) | 16.8 | 2 | 3 | 3 | 3 | 2 | 2 |
| Aluminum acetate | (152) | 16.8 | 3 | 4 | 4 | 4 | 3 | 5 |
| Aluminum lactate | (152) | 16.8 | 2 | 4 | 3 | 3 | 2 | 4 |
| Calcium formate | (337) | 16.8 | 3 | 5 | 2 | 2 | 2 | 4 |
| Calcium citrate | (337) | 16.8 | 5 | 5 | 4 | 5 | 4 | 5 |
| Calcium phosphinate | (337) | 16.8 | 5 | 5 | 3 | 4 | 3 | 4 |
| Calcium lactate | (337) | 16.8 | 5 | 5 | 4 | 3 | 4 | 4 |
| Calcium propionate | (168) | 8.4 | 3 | 4 | 4 | 4 | 3 | 4 |
| | (337) | 16.8 | 3 | 4 | 4 | 3 | 3 | 4 |
| Calcium salicylate | (168) | 8.4 | 4 | 5 | 3 | 4 | 4 | 5 |
| | (337) | 16.8 | 4 | 5 | 4 | 4 | 4 | 4 |
| Fosetyl aluminum salt | (76) | 8.4 | 4 | 4 | 4 | 4 | 4 | 4 |
| | (152) | 16.8 | 4 | 3 | 3 | 3 | 3 | 3 |
| Phosphonic acid monoisopropyl ester aluminum salt | (76) | 8.4 | 4 | 4 | 4 | 4 | 2 | 4 |
| | (152) | 16.8 | 4 | 4 | 4 | 4 | 2 | 4 |
| Fosetyl barium salt | (82) | 1.2 | 4 | 4 | 4 | 4 | 4 | 4 |
| | (164) | 2.4 | 4 | 4 | 4 | 3 | 3 | 4 |
| Aluminum sulfate (comparison) | (76) | 8.4 | D | D | D | D | D | D |
| | (152) | 16.8 | D | 5 | D | 4 | D | D |
| Calcium carbonate (comparison) | (168) | 8.4 | D | D | D | D | D | D |
| | (337) | 16.8 | D | D | D | D | 4 | D |

(Test 2)
Plant Growth Retarding Effects by Glyphosate+Metal Salt
(Test on Dosage Range Applicable for Plant Growth Retardation)

In a 4×4×4 cm$^3$ plastic pot filled with Kureha horticultural soil, seeds of barnyardgrass were sowed and grown for 7 to 10 days in a green house. Wettable powders or liquid preparations having the below-described metal salts incorporated therein were prepared respectively in accordance with Example 1 or Example 5, followed by dilution with water, whereby spray solutions were prepared. The spray solutions were sprayed to each plant. The spray solutions were each adjusted so that an amount of the glyphosate isopropylamine salt might be 62.5, 125, 250, 500, 1000, 2000 or 3000 g ai/ha and the ion equivalent of the metal salt (=the mole concentration of the metal ion in the spray solution×positive valency of the metal) might be 4.2, 8.4 or 16.8 mM. The sprayed volume was set at 1 ml per pot. For comparison, tests were made using a composition containing a single preparation of glyphosate isopropylamine salt, glyphosate aluminum salt (glyphosate/aluminum=4/1 [molar ratio] prepared in accordance with the method described in Japanese Unexamined Publication No. Sho 59-101500) and aluminum sulfate, calcium sulfate, calcium acetate, magnesium chloride, magnesium nitrate or magnesium sulfate as a metal salt. After 7 to 10 days from the spraying, the degree of death and the height of the living plant were measured. From the measured values, "the amount of glyphosate in the mixture permitting the exhibition of effective plant growth retarding effects" was calculated in accordance with the below-described standard and based on the below-described equations 1 and 2, "the range of amount of glyphosate in the mixture permitting the exhibition of effective plant growth retarding effects" and "the ratio of the effective range of amount of glyphosate in the mixture to that of the single glyphosate preparation" were determined. The results are shown in Table 3.

Standard 1: "The amount of glyphosate in the mixture permitting the exhibition of effective plant growth retarding effects" is designated as an amount of glyphosate which satisfies the following two conditions:
(1) concerning growth in plant height, the amount which inhibits at least 70% of the growth in plant height compared with that in the untreated plot, and
(2) concerning the degree of death, the amount at which the death ratio of the test plant is 10% or less.

Equation 1: "The range of amount of glyphosate in the mixture permitting the exhibition of effective plant growth retarding effects"="upperlimit of the amount of glyphosate in the mixture permitting the exhibition of effective plant growth retarding effects"/"lowerlimit of the amount of glyphosate in the mixture permitting the exhibition of effective plant growth retarding effects".

Equation 2: "The ratio of the effective range of amount of glyphosate in the mixture to that of a single glyphosate preparation"="the range of amount of glyphosate in the mixture permitting the exhibition of effective plant growth retarding effects"/"the range of amount of a single glyphosate preparation permitting the exhibition of the effective plant growth retarding effects".

TABLE 3

| Metal salt to be mixed with glyphosate (concentration in terms of metal ion: ppm) | | Ion equiva- lent (mM) | Ratio of effective range of amount of glyphosate in the mixture to that of a single glyphosate preparation |
| --- | --- | --- | --- |
| Fosetyl aluminum salt | (76) | 8.4 | 2.8 |
| | (152) | 16.8 | 2.9 |
| Aluminum nitrate | (76) | 8.4 | 5.4 |
| | (152) | 16.8 | 5.2 |
| Calcium propionate | (168) | 8.4 | 2.0 |
| Calcium citrate | (168) | 8.4 | 6.8 |
| Calcium lactate | (337) | 16.8 | 3.0 |
| Calcium phosphinate | (84) | 4.2 | 2.1 |
| | (169) | 8.4 | 2.4 |
| | (338) | 16.8 | 2.0 |
| Magnesium lactate | (51) | 4.2 | 2.5 |
| | (102) | 8.4 | 4.1 |
| | (204) | 16.8 | 4.2 |

TABLE 3-continued

| Metal salt to be mixed with glyphosate (concentration in terms of metal ion: ppm) | | Ion equivalent (mM) | Ratio of effective range of amount of glyphosate in the mixture to that of a single glyphosate preparation |
|---|---|---|---|
| Magnesium ethoxide | (51) | 4.2 | 2.7 |
| | (102) | 8.4 | 2.4 |
| | (204) | 16.8 | 4.2 |
| Magnesium citrate | (51) | 4.2 | 4.2 |
| | (102) | 8.4 | 2.2 |
| | (204) | 16.8 | 2.8 |
| Aluminum sulfate | (76) | 8.4 | 1.4 |
| (comparison) | (152) | 16.8 | 1.1 |
| Calcium sulfate | (84) | 4.2 | 0.9 |
| (comparison) | (169) | 8.4 | 1.1 |
| | (337) | 16.8 | 1.0 |
| Calcium acetate | (168) | 8.4 | 0.9 |
| (comparison) | | | |
| Magnesium chloride | (51) | 4.2 | 1.0 |
| (comparison) | (102) | 8.4 | 1.6 |
| Magnesium nitrate | (51) | 4.2 | 1.7 |
| (comparison) | (102) | 8.4 | 1.2 |
| Magnesium sulfate | (51) | 4.2 | 1.1 |
| (comparison) | (102) | 8.4 | 1.0 |
| Glyphosate aluminum salt alone (comparison) | | | 1.1 |

(Test 3)
Plant Growth Retarding Effects by Glyphosate+Metal Salt
(Test on the Range of Application Rate for Plant Growth Retardation)

In a 5×150 cm$^3$ plastic pot filled with Kureha horticultural soil, seeds of green foxtail, Johnsongrass, Italian ryegrass, annual bluegrass and barnyardgrass were sowed and grown for 10 days in a green house. Liquid preparations having the below-described metal salts incorporated therein were prepared respectively in accordance with Example 5 and were sprayed to each plant. Upon preparation, the spray solutions were each adjusted so that the amount of the glyphosate isopropylamine salt to be sprayed might be 62.5, 125, 250, 500, 1000, 2000 or 3000 g ai/ha and ion equivalent of the metal salt (the mole concentration of the metal ion in each spray solution×positive valency of the metal) might be 4.2, 8.4 or 16.8 mM. The sprayed amount was set at 1000 liters/ha. For comparison, tests were made using a single preparation of glyphosate isopropylamine salt free from a metal salt, glyphosate aluminum salt (glyphosate/aluminum=4/1 [molar ratio] prepared in accordance with the method described in Japanese Unexamined Patent Publication No. Sho 59-101500) and a composition containing magnesium chloride, magnesium nitrate, calcium nitrate or calcium chloride as a metal salt. After 8 days from the spraying, the degree of death of each plant and the height of the living plant were measured and plant growth retarding effects were studied. In the case where every kind of the plants remained without being killed and the growth of the plant height was controlled by 50 to 99% compared with that in the untreated plot, plant growth retarding effects were evaluated as excellent and represented by O and the other case was represented by X. The results are shown in Table 4.

TABLE 4

| Metal salt to be mixed with glyphosate | Metal ion cocentration (ppm) | Ion equivalent (mM) | Plant growth retarding effects Amount of glyphosate (g/ha) | | | | | | |
|---|---|---|---|---|---|---|---|---|---|
| | | | 62.5 | 125 | 250 | 500 | 1000 | 2000 | 3000 |
| None (single glyphosate preparation) | | | X | X | O | O | X | X | X |
| Calcium citrate | 168 | 8.4 | X | X | X | O | O | X | X |
| | 337 | 16.8 | X | O | O | O | O | X | X |
| Magnesium citrate | 102 | 8.4 | X | X | O | O | X | X | X |
| | 204 | 16.8 | X | O | O | O | O | X | X |
| Calcium propionate | 168 | 8.4 | X | X | X | O | O | X | X |
| | 337 | 16.8 | X | X | X | O | O | O | O |
| Aluminum nitrate | 152 | 16.8 | X | X | X | O | O | O | X |
| Magnesium chloride (comparison) | 102 | 8.4 | X | X | X | O | X | X | X |
| | 204 | 16.8 | X | X | X | O | X | X | X |
| Magnesium nitrate (comparison) | 102 | 8.4 | X | X | X | X | X | X | X |
| | 204 | 16.8 | X | X | X | X | O | X | X |
| Calcium nitrate (comparison) | 168 | 8.4 | X | X | X | X | O | X | X |
| | 336 | 16.8 | X | X | X | X | O | X | X |
| Calcium chloride (comparison) | 168 | 8.4 | X | X | X | X | X | X | X |
| | 337 | 16.8 | X | X | X | O | O | X | X |
| Glyphosate aluminum salt alone (comparison) | | | X | X | X | X | O | O | X |

(Test 4)
Plant Growth Retarding Effects by Glyphosate+Fosetyl Aluminum Salt

In a plastic pot filled with culture soil, seeds of annual bluegrass, Italian ryegrass, Johnsongrass, prickly sida, velvetleaf, wild mustard and morningglory were sowed and grown for 10 days in a green house. Liquid preparations obtained in accordance with Example 4 were tank-mixed and sprayed to the bud of each plant. The sprayed liquids were adjusted so that the concentration of fosetyl aluminum salt might be 2000 ppm, that of glyphosate isopropylamine salt might be 1000 ppm and that of maleic hydrazide choline salt might be 3000 ppm and they were sprayed to wet the plant sufficiently. After 14 and 21 days, the height of each of the weeds was measured. The results are illustrated in Table 5. Incidentally, Gly, F and M denote glyphosate isopropylamine salt, fosetyl aluminum salt and maleic hydrazide choline salt, respectively and the efficacy of each agent is illustrated by the average weed height after 14 and 21 days from the spraying. In the table, 0 cm in the weed height means that the weed is killed.

TABLE 5

| | Average weed height (cm) | |
|---|---|---|
| Active ingredient (ppm) | After 14 days | After 21 days |
| Gly (1000) + F (2000) | 7 | 17 |
| Gly (1000) + F (2000) + M (3000) | 5 | 7 |
| Gly (1000) | 0 | 0 |
| M (3000) | 9 | 20 |
| Untreated | 14 | 24 |

In the levee between rice fields in Japan, weeds growing to the height of at least about 20 cm are mowed because they hinder farming work. To completely kill weeds by a herbicide or the like is, on the other hand, not desired, because it leads to landslide of the levee between rice fields. In addition, the weed control is required for about 6 months from about April to October.

As is apparent from Table 5, the glyphosate isopropylamine salt killed weeds and did not exhibit plant growth retarding effects when used singly. The mixture of it with fosetyl aluminum salt retarded the plant growth without killing weeds. These plant growth retarding effects were maintained longer by incorporating maleic hydrazide choline salt with the above mixture.

Since the composition containing maleic hydrazide choline salt exhibits plant growth retarding effects and does not kill even the root of the plant, the levee between the rice fields are not destroyed by landslide. In addition, the incorporation of it extends the growth retarding time, which contributes to labor saving. Such a composition is therefore desired also from the economical viewpoint.

(Test 5)
Plant Growth Retarding Effects by Glyphosate+Fosetyl Aluminum Salt or Calcium Propionate In a 5×150 cm$^3$ plastic pot filled with Kureha horticultural soil, seeds of gramineous weeds (green foxtail, Johnsongrass, Italian ryegrass, barnyardgrass) and broadleaf weeds (prickly sida, velvetleaf, wild mustard and ragweed) were sowed and grown for 14 days in a green house. Wettable powders or liquid preparations were prepared respectively in accordance with Example 1 or Example 6, followed by dilution with water, whereby spray solutions were prepared. The stem and leaf of above-described weeds were sprayed with each of the spray solutions. Upon preparation, each of the spray solutions was adjusted so that the amount of glyphosate isopropylamine salt might be 0.125, 0.25, 0.5, 1 and 2 kg/ha; that of fosetyl aluminum salt might be 2 and 4 kg/ha; that of maleic hydrazide might be 1.5 and 3 kg/ha; and that of calcium propionate salt might be 1.5 and 3 kg/ha. The sprayed amount was set at 1000 liters/ha. After 21 days from the spraying, the degree of death of the plant and the height of living plant were measured and plant growth retarding effects were determined. The results are shown in Table 7. The plant growth retarding effects are illustrated by a numeral or a letter of the alphabet and the numeral or letter of the alphabet indicated the height suppressing rate shown in Table 6. In the table, Gly, F, MH, P, f, J, I, b, p, v, w and r denote glyphosate isopropylamine salt, fosetyl aluminum salt, maleic hydrazide, calcium propionate, green foxtail, Johnsongrass, Italian ryegrass, barnyardgrass, prickly sida, velvetleaf, wild mustard and ragweed, respectively.

TABLE 6

| Plant growth retarding effects | Plant height suppressing ratio (%) |
|---|---|
| D | 100 (complete death) |
| 9 | 90–99 |
| 8 | 80–89 |
| 7 | 70–79 |
| 6 | 60–69 |
| 5 | 50–59 |
| 4 | 40–49 |
| 3 | 30–39 |
| 2 | 20–29 |
| 1 | 10–19 |
| 0 | 0–9 |

TABLE 7

| | Plant growth retarding effects | | | | | | | | |
|---|---|---|---|---|---|---|---|---|---|
| | Gramineous weeds | | | | Broadleaf weeks | | | | Number of kind of |
| Active ingredient (kg ai/ha) | f | J | I | b | p | v | c | w | Average | dead weed |
| Gly(0.125) | 5 | 4 | 3 | 5 | 0 | 0 | 2 | 0 | 2 | 0 |
| Gly(0.25) | 6 | 6 | 5 | 5 | 3 | 2 | 5 | 5 | 5 | 0 |
| Gly(0.5) | D | D | 8 | 8 | 7 | 7 | 8 | D | 8 | 3 |
| Gly(1) | D | D | D | D | 8 | 8 | 8 | D | 8 | 5 |
| Gly(2) | D | D | D | D | D | D | D | D | D | 8 |
| Gly(1) + F(2) | 8 | 3 | 4 | 4 | 4 | 3 | 4 | 5 | 4 | 0 |
| Gly(2) + F(4) | 9 | 8 | 2 | 4 | 7 | 4 | 4 | 5 | 5 | 0 |

TABLE 7-continued

| | Plant growth retarding effects | | | | | | | | | |
|---|---|---|---|---|---|---|---|---|---|---|
| Active ingredient | Gramineous weeds | | | | Broadleaf weeks | | | | | Number of kind of |
| (kg ai/ha) | f | J | I | b | p | v | c | w | Average | dead weed |
| Gly(1) + F(2) + MH(1.5) | 9 | 7 | 7 | 6 | 7 | 8 | 9 | 7 | 7 | 0 |
| Gly(2) + F(4) + MH(3) | 9 | 9 | 7 | 8 | 7 | 8 | 9 | 7 | 8 | 0 |
| F(2) | 0 | 0 | 0 | 0 | 0 | 0 | 0 | 0 | 0 | 0 |
| F(4) | 0 | 0 | 0 | 0 | 0 | 0 | 0 | 0 | 0 | 0 |
| Gly(1) + MH(1.5) | D | D | D | D | D | D | D | D | D | 8 |
| Gly(2) + MH(3) | D | D | D | D | D | D | D | D | D | 8 |
| F(2) + MH(1.5) | 0 | 0 | 2 | 0 | 4 | 3 | 5 | 1 | 2 | 0 |
| F(4) + MH(3) | 0 | 0 | 4 | 0 | 6 | 5 | 6 | 3 | 3 | 0 |
| MH(1.5) | 3 | 2 | 3 | 0 | 6 | 2 | 6 | 4 | 3 | 0 |
| MH(3) | 4 | 3 | 5 | 0 | 6 | 5 | 6 | 3 | 4 | 0 |
| Gly + (0.25) + P(1.5) | 7 | 4 | 5 | 4 | 2 | 2 | 5 | 5 | 4 | 0 |
| Gly(0.5) + P(3) | 8 | 5 | 7 | 4 | 5 | 2 | 6 | 5 | 5 | 0 |
| Gly(0.25) + P(1.5) + MH(1.5) | 9 | 6 | 7 | 5 | 7 | 6 | 6 | 6 | 7 | 0 |
| Gly(0.5) + P(3) + MH(3) | 6 | 5 | 7 | 5 | 5 | 5 | 6 | 5 | 6 | 0 |
| P(1.5) | 0 | 0 | 0 | 0 | 0 | 0 | 0 | 0 | 0 | 0 |
| P(3) | 0 | 0 | 0 | 0 | 0 | 0 | 0 | 0 | 0 | 0 |
| Gly(0.25) + MH(1.5) | 5 | 6 | 4 | 4 | 4 | 1 | 5 | 4 | 4 | 0 |
| Gly(0.5) + MH(3) | D | 9 | 9 | D | 8 | 8 | D | D | 9 | 4 |
| P(1.5) + MH(1.5) | 2 | 2 | 2 | 0 | 6 | 2 | 5 | 4 | 3 | 0 |
| P(3) + MH(3) | 4 | 3 | 4 | 0 | 6 | 4 | 5 | 3 | 4 | 0 |

(Test 6)
Plant Growth Retarding Effects by Glyphosate+Chitosan

In a plastic pot filled with culture soil, seeds of annual bluegrass and Italian ryegrass were sowed and grown for 10 days in a green house. Liquid preparations prepared in accordance with Example 9 were each tank-mixed and sprayed to the bud of each plant. The concentration of chitosan (water soluble chitosan, product of Wako Pure Chemicals, Inc.) in the spray solution was adjusted to 10,000 ppm, 20,000 ppm or 40,000 ppm, while that of glyphosate isopropylamine salt was adjusted to 1,000 ppm. The spray solution was sprayed to wet the plant sufficiently. After 14 and 21 days from the spraying, the height of each weed was measured. The results are illustrated in Table 8.

Incidentally, in the table, Gly and C indicate glyphosate isopropylamine salt and chitosan, respectively and efficacy of the agent is determined by the height (cm) after 14 and 21 days from the spraying.

TABLE 8

| | After 14 days | | After 21 days | |
|---|---|---|---|---|
| Active ingredient | Annual bluegrass | Ryegrass | Annual bluegrass | Ryegrass |
| Gly 1000 ppm + C 10000 ppm | 3 | 10 | 10 | 19 |
| Gly 1000 ppm + C 20000 ppm | 2 | 10 | 6 | 16 |
| Gly 1000 ppm + C 40000 ppm | 3 | 10 | 6 | 17 |
| Gly 1000 ppm | 0 | 0 | 0 | 0 |
| Untreated plot | 7 | 31 | 11 | 38 |

The above results of Test 6 indicate that a mixture of chitosan and glyphosate retards the growth of a plant without killing it.

(Test 7)
Plant Growth Retarding Effects by Glyphosate+Chitosan

In a 5×150 cm³ plastic pot filled with Kureha horticultural soil, seeds of annual bluegrass and Italian ryegrass were sowed and grown for 10 days in a green house, followed by spraying to stem and leaf of each plants with liquid preparations prepared in accordance with Example 9. Upon preparation, the spray solutions were each adjusted so that the concentration of chitosan (water soluble chitosan; product of Wako Pure Chemicals, Inc.) might be 2500, 5000, 10000, 20000 or 40000 ppm and the concentration of glyphosate isopropylamine salt might be 250, 500 or 1000 ppm. The sprayed volume was set at 1000 liters/ha. After 14 and 20 days from the spraying, the height of weeds were measured and plant growth retarding effects were determined. The results are shown in Table 9. Incidentally, Gly and C denote glyphosate isopropylamine salt and chitosan, respectively and plant growth retarding effects are determined by the weed height (cm) after 14 and 21 days from the spraying.

TABLE 9

| | Plant growth retarding effects (height of weed, cm) | | | |
|---|---|---|---|---|
| | After 14 days | | After 20 days | |
| Active ingredient (concentration, ppm) | Annual bluegrass | Italian ryegrass | Annual bluegrass | Italian ryegrass |
| Gly(250) + C(2500) | 4 | 10 | 7 | 14 |
| Gly(250) + C(5000) | 4 | 10 | 8 | 12 |
| Gly(250) + C(10000) | 4 | 10 | 6 | 12 |
| Gly(500) + C(5000) | 4 | 9 | 6 | 10 |
| Gly(500) + C(10000) | 4 | 9 | 5 | 10 |
| Gly(500) + C(20000) | 4 | 9 | 5 | 10 |
| Gly(1000) + C(10000) | 3 | 8 | 6 | 10 |
| Gly(1000) + C(20000) | 3 | 8 | 5 | 10 |
| Gly(1000) + C(40000) | 3 | 8 | 5 | 9 |
| Gly(250) | 4 | 10 | 8 | 14 |
| Gly(500) | 4 | 7 | 7 | 9 |
| Gly(1000) | 0 | 0 | 0 | 0 |
| C(2500) | 8 | 25 | 11 | 28 |
| C(5000) | 8 | 25 | 11 | 28 |
| C(10000) | 8 | 25 | 11 | 28 |
| C(20000) | 8 | 25 | 11 | 28 |

TABLE 9-continued

| | Plant growth retarding effects (height of weed, cm) | | | |
|---|---|---|---|---|
| | After 14 days | | After 20 days | |
| Active ingredient (concentration, ppm) | Annual bluegrass | Italian ryegrass | Annual bluegrass | Italian ryegrass |
| C(40000) | 8 | 25 | 11 | 28 |
| Untreated plot | 8 | 25 | 11 | 28 |

(Test 8)
Crop Selective Herbicidal Effects by Glyphosate or Glufosinate+Fosetyl Aluminum Salt In a plastic pot (5×150 cm$^3$) filled with culture soil, seeds of corn, soybean, cotton, gramineous weeds (annual bluegrass, Italian ryegrass, Johnsongrass and barnyard grass) and broadleaf weeds (prickly sida, velvetleaf, wild mustard and morningglory) were sowed and grown for 14 days in a green house, followed by spraying to stem and leaf to each plant with liquid preparations prepared in accordance with Example 3. The spray solutions were each adjusted so that the concentration of glyphosate isopropylamine salt might be 500 or 1000 ppm, that of glufosinate ammonium might be 150 or 300 ppm and that of fosetyl aluminum salt might be 1000, 2000 or 3000 ppm. The spraying was carried out to wet each plant completely. After 14 days from the spraying, the efficacy of the agent was observed and determined. The results are shown in Table 10. Incidentally, in the table, Gly, Glu and F denote glyphosate isopropylamine salt, glufosinate ammonium and fosetyl aluminum salt, respectively. Efficacy of the agent is illustrated by 0 to 10 stages, wherein 0 means no efficacy, while 10 means complete death. The crop injury from the agents is ranked by four stages from − to +++, wherein − means no crop injury and +++ means serious crop injury. D means that dead weed was observed.

TABLE 10

| Active ingredient (ppm) | Gramineous weeds | Broadleaf weeds | Corn | Soy-bean | Cotton |
|---|---|---|---|---|---|
| Gly(1000) + F(1000) | 7D | 5D | ++ | + | + |
| Gly(1000) + F(2000) | 5 | 5 | ++ | − | − |
| Gly(1000) + F(3000) | 4 | 4 | − | − | − |
| Glu(300) + F(1000) | 5D | 9D | + | ++ | ++ |
| Gly(1000) | 9D | 8D | +++ | +++ | +++ |
| Gly(500) | 7D | 5D | +++ | +++ | +++ |
| Glu(300) | 9D | 10D | +++ | +++ | +++ |
| Glu(150) | 6D | 9D | +++ | +++ | +++ |

As shown in Table 10, the single preparation of glyphosate isopropylamine salt or that of glufosinate ammonium has high herbicidal effects but crop selectivity was not observed at all.

When glyphosate isopropylamine salt or glufosinate ammonium is mixed with fosetyl aluminum salt, the herbicidal activity shows a slight deterioration compared with the single preparation, but marked effects for reducing crop injury from the agents are brought about for soybean and cotton in using glyphosate and for corn in using glufosinate. In short, the herbicides are given selectivity between crop and weed by mixing. This is apparent from a marked difference in the crop injury from the agents between the composition of the present invention and the single preparation of glyphosate isopropylamine salt or glufosinate ammonium when the herbicidal effects are equal.

(Test 9)
Crop Selective Herbicidal Effects by Glufosinate+Metal Salt

In a 5×150 cm$^3$ plastic pot filled with Kureha horticultural soil, seeds of corn, wheat, rice, gramineous weeds (green foxtail, Johnsongrass, Italian ryegrass, barnyard grass) and broadleaf weeds (prickly sida, velvetleaf, wild mustard and morningglory) were sowed and grown for 14 days in a green house. Wettable powders or liquid preparations were prepared in accordance with Example 14 or Example 15, followed by dilution with water, whereby spray solutions were prepared. Each plant was subjected to spray to stem and leaf of each plant with the spray solutions. Upon preparation, each of the spray solutions was adjusted so that the concentration of glufosinate aluminum might be 50, 100, 150 or 200 ppm and the ion concentration of aluminum, iron or calcium derived from each metal salt (fosetyl aluminum salt, fosetyl iron salt, calcium acetate salt, calcium levulinate salt or calcium benzoate salt) might be 40, 80 or 160 ppm. The sprayed volume was set at 1000 liters/ha. After 14 days from the spraying, the herbicidal effects and the degree of crop injury from the agents were observed and determined. The results are shown in Table 11. Herbicidal effects are illustrated by a numeral, while the degree of crop injury from the agents is expressed by a symbol. The herbicidal effects are ranked by 6 stages from 0 to 5, wherein 0 indicates the height growth suppressing ratio less than 10% and 5 indicates the height growth suppressing ratio of 90% or greater. The crop injury from the agents is ranked by four symbol from − to +++, wherein − indicates no crop injury and +++ indicates serious crop injury. In the table, Glu, gramineous, broadleaf, c, w and r denote glufosinate ammonium, average of gramineous weeds, average of broadleaf weeds, corn, wheat and rice, respectively.

TABLE 11

| Active ingredient (concentration, ppm) | Herbicidal effects | | Degree of crop injury | | |
|---|---|---|---|---|---|
| | Gramineous | Broadleaf | c | w | r |
| Glu (50) | 1 | 3 | − | − | − |
| Glu (100) | 2 | 4 | + | + | + |
| Glu (150) | 3 | 5 | ++ | +++ | +++ |
| Glu (200) | 4 | 5 | +++ | +++ | +++ |
| Glu (150) + fosetyl aluminum salt (40) | 2 | 5 | − | − | − |
| Glu (150) + fosetyl aluminum salt (80) | 1 | 5 | − | − | − |
| Glu (150) + fosetyl iron salt (40) | 3 | 4 | − | − | + |
| Glu (150) + fosetyl iron salt (80) | 3 | 4 | − | − | + |
| Glu (150) + calcium acetate salt (80) | 3 | 5 | − | + | + |
| Glu (150) + calcium acetate salt (160) | 3 | 5 | − | + | + |
| Glu (150) + calcium levulinate salt (80) | 2 | 4 | − | − | + |
| Glu (150) + calcium levulinate salt (160) | 3 | 4 | − | − | + |
| Glu (150) + calcium benzoate salt (80) | 2 | 4 | − | − | + |
| Glu (150) + calcium benzoate salt (160) | 2 | 4 | − | − | + |

(Test 10)
Crop Selective Herbicidal Effects by Glyphosate+Phosphorous Acid Derivative In a 5×150 cm$^3$ plastic pot filled with Kureha horticultural soil, seeds of soybean, cotton, gramineous weeds (green foxtail, Johnsongrass, Italian ryegrass, barnyardgrass) and broadleaf weeds (prickly sida, velvetleaf, wild mustard and ragweed) were sowed and grown for 14 days in a green house. Wettable powders were prepared in accordance with Example 1, followed by dilution with water, whereby spray solutions were prepared. The stem and leaf of each of the plants was subjected to spray with the spray solutions. Upon preparation, the spray solutions were each adjusted so that the concentration of glyphosate isopropylamine salt might be 250, 500 or 1000 ppm and the ion concentration of aluminum or iron derived from phosphorus acid derivative might be 80 or 160 ppm. After 14 days from the spraying, the herbicidal effects and the degree of crop injury from the agents were observed and determined. The results are shown in Table 12. Herbicidal effects are illustrated by a numeral, while the degree of crop injury are expressed by a symbol. Herbicidal effects are ranked by 6 stages from 0 to 5, wherein 0 indicates the height growth suppressing ratio less than 10% and 5 indicates the height growth suppressing ratio of 90% or greater. The crop injury from the agents is ranked by four stages from − to +++, wherein − indicates no crop injury and +++ indicates serious crop injury. In the table, Gly, gramineous and broadleaf mean glyphosate isopropylamine salt, average of gramineous weeds and average of broadleaf weeds, respectively.

TABLE 12

| Active ingredient | Herbicidal effects | | Degree of crop injury | |
| --- | --- | --- | --- | --- |
| (concentration ppm) | Gramineous | Broadleaf | Soybean | Cotton |
| Gly (250) | 3 | 3 | ++ | + |
| Gly (500) | 4 | 4 | +++ | ++ |
| Gly (1000) | 5 | 5 | +++ | +++ |
| Gly (1000) + fosetyl aluminum salt (80) | 4 | 3 | + | + |
| Gly (1000) + fosetyl aluminum salt (160) | 3 | 3 | − | − |
| Gly (1000) + fosetyl iron salt (160) | 3 | 3 | + | − |

(Test 11)
Corn Selective Herbicidal Effects of Glufosinate+Fosetyl Aluminum Salt+Atrazine In a 5×150 cm$^3$ plastic pot filled with Kureha horticultural soil, seeds of corn, gramineous weeds (green foxtail, Johnsongrass, Italian ryegrass, barnyardgrass) and broadleaf weeds (prickly sida, velvetleaf, wild mustard and morningglory) were sowed and grown for 14 days in a green house. Wettable powders were prepared in accordance with Example 16, followed by dilution with water, whereby spray solutions were prepared. The stem and leaf of each plant was subjected to spray with the spray solutions. Upon preparation, the spray solutions were each adjusted so that the concentration of glufosinate ammonium might be 100 or 200 ppm, that of fosetyl aluminum salt might be 1000 or 2000 ppm and that of atrazine might be 500, 1000 or 2000 ppm. The sprayed amount was set at 1000 liters/ha. After 14 days from the spraying, the herbicidal effects and the degree of crop injury from the agents were observed and determined. The results are shown in Table 13. The herbicidal effects are illustrated by a numeral, while the degree of crop injury is illustrated by a symbol. The herbicidal effects are ranked by 6 stages from 0 to 5, wherein 0 indicates the height growth suppressing ratio less than 10% and 5 indicates the height growth suppressing ratio of 90% or greater. The crop injury from the agents is ranked by four symbols from − to +++, wherein − indicates no crop injury and +++ indicates serious crop injury. In the table, Glu, F, A, gramineous and broadleaf denote glufosinate ammonium, fosetyl aluminum salt, atrazine, average of gramineous weeds and average of broadleaf weeds, respectively.

TABLE 13

| Active ingredient | Herbicidal effects | | Degree of crop injury |
| --- | --- | --- | --- |
| (concentration, ppm) | Gramineous | Broadleaf | Corn |
| Glu(100) + A(500) + F(1000) | 3 | 5 | − |
| Glu(200) + A(1000) + F(2000) | 4 | 5 | − |
| Glu(100) + A(1000) + F(1000) | 4 | 5 | − |
| Glu(200) + A(2000) + F(2000) | 5 | 5 | − |
| Glu(100) | 2 | 3 | − |
| Glu(200) | 3 | 4 | + |
| A(500) | 2 | 4 | − |
| A(1000) | 2 | 4 | − |
| A(2000) | 3 | 5 | − |
| Glu(100) + A(500) | 3 | 5 | − |
| Glu(200) + A(1000) | 4 | 5 | + |
| Glu(100) + A(1000) | 3 | 5 | − |
| Glu(200) + A(2000) | 4 | 5 | + |
| A(500) + F(1000) | 2 | 4 | − |
| A(1000) + F(2000) | 2 | 4 | − |
| A(1000) + F(1000) | 2 | 4 | − |
| A(2000) + F(2000) | 3 | 5 | − |

(Test 12)
Crop Selective Herbicidal Effects by Glyphosate+Chitosan

In a plastic pot filled with soil, seeds of soybean, cotton, gramineous weeds (green foxtail, Johnsongrass, crabgrass, barnyardgrass) and broadleaf weeds (prickly sida, velvetleaf, wild mustard, ragweed and morningglory) were sowed and grown for 14 days in a green house. Liquid preparations prepared in accordance with Example 9 were tank-mixed and sprayed to the bud of each plant. Upon preparation, the spray solutions were each adjusted so that the concentration of chitosan might be 20,000 ppm, that of glyphosate isopropylamine salt might be 1,000 ppm and that of glyphosate trimethylsulfonium salt might be 500 ppm. It was sprayed to wet each plant sufficiently. After 14 days from the spraying, the efficacy of the herbicide was observed and determined. The results are shown in Table 14. In the table, Gly, S and C denote glyphosate isopropylamine salt, glyphosate trimethylsulfonium salt and chitosan, respectively. The herbicidal efficacy is illustrated by 0 to 10 stages, wherein 0 indicates no efficacy and 10 indicates complete death. D means that generation of dead weeds was observed.

TABLE 14

| Active ingredient | Gramineous weeds | Broadleaf weeds | Soybean | Cotton |
| --- | --- | --- | --- | --- |
| Gly + C | 8 | 6 | 1 | 1 |
| Gly | 9D | 8D | 8 | 5 |
| S + C | 6 | 6 | 1 | 1 |
| S | 9D | 9D | 9 | 9 |

The above results of Test 12 show that crop injury from glyphosate, particularly to soybean and cotton, was markedly reduced by chitosan.

(Test 13)
Corn Selective Herbicidal Effects by Glufosinate or Bialaphos+Chitosan In a plastic pot filled with culture soil, corn, gramineous weeds (green foxtail, Johnsongrass, crabgrass and barnyardgrass) and broadleaf weeds (prickly sida, velvetleaf, wild mustard, ragweed and morningglory) were sowed and grown for 14 days in a green house. Liquid preparations prepared in accordance with Example 12 were tank-mixed and sprayed to the bud of each plant. The concentration of chitosan (water soluble chitosan, product of Wako Pure Chemicals, Inc.) in the spray solutions was adjusted to 500 or 1000 ppm, that of glufosinate ammonium to 150 or 200 ppm and that of bialaphos sodium salt to 200 ppm. Spraying was carried out to wet each of the plants sufficiently. After 14 days from the spraying, the herbicidal efficacy was observed and determined. The results are shown in Table 15. In the table, C, Glu and B denote chitosan, glufosinate ammonium and bialaphos sodium salt, respectively. The efficacy of the herbicide is illustrated by 0 to 10 stages, wherein 0 indicates no efficacy and 10 indicates complete death.

TABLE 15

| Active ingredient (ppm) | Herbicidal effects | | Crop injury Corn |
|---|---|---|---|
| | Gramineous weeds | Broadleaf weeds | |
| Glu (150) | 9 | 9 | 3 |
| Glu (200) | 10 | 10 | 5 |
| Glu (150) + C (1000) | 8 | 8 | 0 |
| Glu (200) + C (1000) | 9 | 9 | 2 |
| B (200) | 7 | 8 | 3 |
| B (200) + C (500) | 7 | 8 | 1 |
| B (200) + C (1000) | 7 | 8 | 1 |
| C (1000) | 0 | 0 | 0 |

As shown in Table 15, chitosan can markedly reduce crop injury, particularly corn, without impairing high herbicidal effects of glufosinate ammonium or bialaphos sodium salt against weeds.

(Test 14)

Corn Selective Herbicidal Effects of Glufosinate+Chitosan+Atrazine

In a 5×150 cm$^3$ plastic pot filled with Kureha horticultural soil, seeds of corn, gramineous weeds (green foxtail, Johnsongrass, annual bluegrass, barnyardgrass) and broadleaf weeds (prickly sida, velvetleaf, wild mustard and morningglory) were sowed and grown for 14 days in a green house. Wettable powders were prepared in accordance with Example 17, followed by dilution with water, whereby spray solutions were prepared. The stem and leaf of each of the plants was subjected to spray with the spray solutions. Upon preparation, the spray solutions were each adjusted so that the concentration of glufosinate ammonium might be 100 or 200 ppm, that of water soluble chitosan might be 1000 or 2000 ppm and that of atrazine might be 500, 1000 or 2000 ppm. The sprayed volume was set at 1000 liters/ha. After 14 days from the spraying, the herbicidal effects against weeds and the degree of crop injury from the agents were observed and determined. The results are shown in Table 16. Herbicidal effects are ranked by 6 stages from 0 to 5, wherein 0 indicates the height growth suppressing ratio less than 10% and 5 indicates the height growth suppressing ratio of 90% or greater. The crop injury from the agents is ranked by four symbols from – to +++, wherein – indicates no crop injury and +++ indicates marked crop injury. In the table, Glu, C, A denote glufosinate ammonium, water soluble chitosan and atrazine, respectively.

TABLE 16

| Active ingredient (ppm) | Herbicidal effects | | Crop damage corn |
|---|---|---|---|
| | Gramineous weeds | Broadleaf weeds | |
| Glu (100) + A (500) + C (1000) | 3 | 5 | – |
| Glu (200) + A (1000) + C (2000) | 4 | 5 | – |
| Glu (100) + A (1000) + C (1000) | 4 | 5 | – |
| Glu (200) + A (2000) + C (2000) | 4 | 5 | – |
| Glu (100) | 2 | 3 | – |
| Glu (200) | 2 | 4 | + |
| A (500) | 2 | 4 | – |
| A (1000) | 2 | 4 | – |
| A (2000) | 3 | 5 | – |
| Glu (100) + A (500) | 3 | 5 | – |
| Glu (200) + A (1000) | 4 | 5 | + |
| Glu (100) + A (1000) | 3 | 5 | – |
| Glu (200) + A (2000) | 4 | 5 | + |
| A (500) + C (1000) | 2 | 4 | – |
| A (1000) + C (2000) | 2 | 4 | – |
| A (1000) + C (1000) | 2 | 4 | – |
| A (2000) + C (2000) | 3 | 5 | – |

(Test 15)

Corn Selective Herbicidal Effects of Glufosinate+Chitosan+Atrazine (Cultivating Conditions of Corn on the Supposition of the Corn Belt Zone of North America)

In a 5×150 cm$^3$ plastic pot filled with Kureha horticultural soil, seeds of corn, gramineous weeds (crabweed, Johnsongrass, shattercane, barnyardgrass) and broadleaf weeds (prickly sida, morningglory and redroot pigweed) were sowed and grown in an air-conditioned room set at an average temperature of 22° C. until the height of the corn became 15 cm. Wettable powders were prepared in accordance with Example 18, followed by dilution with water, whereby spray solutions were prepared. The plants were subjected to spray to the stem and leaf of each plants with the spray solutions. Upon preparation, the spray solutions were each adjusted so that the concentration of glufosinate ammonium might be 100, 200, 300 or 400 ppm, that of water soluble chitosan might be 100, 200, 300 or 400 ppm and that of atrazine might be 1000, 2000, 3000 or 4000 ppm. The sprayed volume was set at 1000 liters/ha. On Day 10 after spraying, the herbicidal effects against weeds and the degree of crop injury from the agents were observed and determined. The results are shown in Table 17. The herbicidal effects are illustrated by 6 stages from 0 to 5, wherein 0 indicates the height growth suppressing ratio less than 10% and 5 indicates the height growth suppressing ratio of 90% or greater. The crop injury is ranked by four symbols from – to +++, wherein + indicates no crop injury and +++ indicates serious crop injury. In the table, Glu, C, A denote glufosinate ammonium, water soluble chitosan and atrazine, respectively.

TABLE 17

| Active ingredient (ppm) | Herbicidal effects | | Crop damage corn |
|---|---|---|---|
| | Gramineous weeds | Broadleaf weeds | |
| Glu (100) + A (1000) + C (100) | 5 | 5 | – |
| Glu (200) + A (2000) + C (200) | 5 | 5 | – |
| Glu (300) + A (3000) + C (300) | 5 | 5 | – |
| Glu (400) + A (4000) + C (400) | 5 | 5 | + |
| Glu (100) | 3 | 5 | – |
| Glu (200) | 4 | 5 | – |
| Glu (300) | 4 | 5 | – |
| Glu (400) | 5 | 5 | +++ |

TABLE 17-continued

| Active ingredient (ppm) | Herbicidal effects | | Crop damage corn |
|---|---|---|---|
| | Gramineous weeds | Broadleaf weeds | |
| A (1000) | 2 | 5 | − |
| A (2000) | 2 | 5 | − |
| A (3000) | 2 | 5 | − |
| A (4000) | 2 | 5 | − |
| Glu (100) + A (1000) | 5 | 5 | − |
| Glu (200) + A (2000) | 5 | 5 | − |
| Glu (300) + A (3000) | 5 | 5 | + |
| Glu (400) + A (4000) | 5 | 5 | +++ |

The agricultural chemical composition of the present invention can be used as a plant growth retarding agent.

Described specifically, the composition of the present invention brings about a change in the phytotoxicity (action to kill even the root of a plant) of a nonselective phosphoric acid herbicide, thereby making it possible to retard the plant growth without killing the plant and to use it on a slope or levees between rice fields. The composition of the present invention further comprising maleic hydrazide or the like can maintain plant growth retarding effects for longer time.

By the plant growth retarding action of the agricultural chemical composition of the present invention, the opportunities using a nonselective phosphoric acid herbicides increase.

The agricultural chemical composition of the present invention can also be used as a crop selective herbicide.

Described specifically, the composition of the present invention is designed to chemically reduce the crop injury caused by nonselective phosphoric acid herbicides, which makes them possible to use the nonselective phosphoric acid herbicide as a selective herbicide on crops such as corn, soybean, cotton, wheat, sorghum and rice.

The agricultural chemical composition of the present invention has herbicidal efficacy against gramineous weeds such as annual bluegrass, Italian ryegrass, Johnsongrass, barnyardgrass, green foxtail and fall panicum and broadleaf weeds such as prickly sida, velvetleaf, wild mustard, morningglory, chickweed, cocklebur, henbit, common lambsquarters, goosefoot, ragweed and smartweed. It can be used as a herbicide for these weeds.

The general dosage of herbicides in each crop can be reduced and the herbicidal spectrum can be widened by mixing the agricultural chemical composition of the present invention with another agricultural chemical active ingredient having crop selectivity. In comparison with a composition comprising another agricultural chemical active ingredient having crop selectivity and the above-described nonselective herbicide, the agricultural chemical composition of the present invention has an improved crop selectivity and a wider range of the amount of agents and it becomes a herbicide which can be used in more applied areas.

We claim:

1. An agricultural chemical composition which comprises one or more of a first component (a) having herbicidal activity and one or more of a second component (b) and optionally one or more of a third component (c);
   1 part by weight of said component (a) selected from the group consisting of
   N-(phosphonomethyl)glycine or a salt thereof,
   N,N-bis(phosphonomethyl)glycine or a salt thereof,
   4-(hydroxy(methyl)phosphinoyl)-L-homoalanyl-L-alanyl-L-alanine or a salt thereof, and
   4-(hydroxy(methyl)phosphinoyl)-DL-homoalanine or a salt thereof;
   said component (b) selected from the group consisting of
   (i) 0.001 to 100 parts by weight of a phosphorus acid compound represented by the following formula (I):

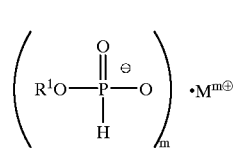

(I)

wherein $R^1$ represents an unsubstituted $C_{1-8}$ alkyl group, a $C_{1-8}$ alkyl group substituted with 1 to 3 halogen atoms or 1 to 3 $C_{1-3}$ alkoxy groups, a phenyl group or a benzyl group; M represents a hydrogen atom, an unsubstituted ammonium group, an ammonium group substituted with 1 to 4 $C_{1-3}$ alkyl groups, a sodium atom, a potassium atom, a lithium atom, a magnesium atom, a calcium atom, a barium atom, a zinc atom, a manganese atom, a copper atom, an iron atom, a nickel atom or an aluminum atom; and m stands for an integer equivalent to the positive valency of M;

(ii) 0.01 to 300 parts by weight of a chitosan compound represented by the following formula (II):

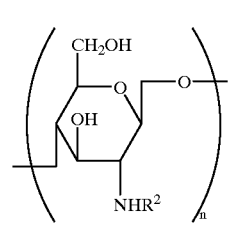

(II)

wherein n stands for an integer of 1 or greater and $R^2$ represents a hydrogen atom, a $C_{1-6}$ alkyl group or a $C_{1-11}$ acyl group;

(iii) 0.001 to 100 parts by weight of an isopropyl phosphate salt selected from the group consisting of a magnesium salt, barium salt, aluminum salt, calcium salt and iron salt of isopropyl phosphate;

(iv) 0.001 to 100 parts by weight of an organic acid metal salt selected from the group consisting of magnesium salts, barium salts, aluminum salts and calcium salts of an organic acid selected from the group consisting of lactic acid, propionic acid, formic acid, acetic acid, levulinic acid, benzoic acid, citric acid, alginic acid, L-(+)-ascorbic acid and salicylic acid, with the proviso that magnesium acetate and calcium acetate are excluded when the component (a) contains N-(phosphonomethyl) glycine or a salt thereof, magnesium ethoxide or aluminum acetyl acetate; and (v) 0.001 to 100 parts by weight of an inorganic metal salt selected from the group consisting of aluminum nitrate, calcium phosphinate, ammonium aluminum sulfate and potassium aluminum sulfate; and 0.1 to 500 parts by weight of said component (c) selected from the group consisting of
a plant growth regulator, a fungicide which is an inhibitor of ergosterol biosynthesis, mefluidide, atrazine, pyridate and clopyralid.

2. The agricultural chemical composition according to claim 1, wherein the component (a) is one or more compound selected from the group consisting of N-(phosphonomethyl)glycine or a salt thereof and 4-(hydroxy(methyl)phosphinoyl)-DL-homoalanine or a salt thereof, and the composition is a plant growth retardant composition.

3. The agricultural chemical composition according to claim 1, wherein the component (a) is N-(phosphonomethyl) glycine or a salt thereof.

4. The agricultural chemical composition according to any one of claims 1 to 3, wherein the component (b) is one or more than one compound selected from the group consisting of:

(i) 0.001 to 100 parts by weight of a phosphorus acid compound represented by the formula (I):

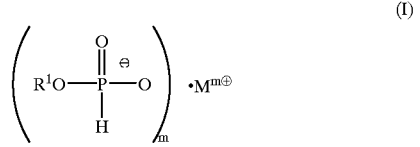

wherein $R^1$ represents a $C_{1-4}$ alkyl group, M represents a magnesium atom, a calcium atom, a barium atom or an aluminum atom and m stands for an integer equivalent to the positive valency of M;

(ii) 0.01 to 300 parts by weight of a chitosan compound represented by the following formula (II):

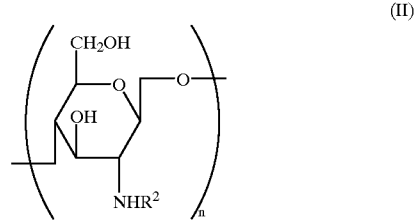

wherein n stands for an integer of 1 or greater and $R^2$ represents a hydrogen atom or an acetyl group;

(iii) 0.001 to 100 parts by weight of the aluminum salt of isopropyl phosphate;

(iv) 0.001 to 100 carts by weight of organic acid metal salt selected from the group consisting of magnesium salts, aluminum salts and calcium salts of one organic acid selected from the group consisting of lactic acid, propionic acid, formic acid, acetic acid, levulinic acid, benzoic acid, citric acid, L-(+)-ascorbic acid and salicylic acid, with the proviso that magnesium acetate and calcium acetate are excluded when the component (a) contains N-(phosphonomethyl)glycine or a salt thereof, and magnesium ethoxide; and 0.001 to 100 parts by weight of an inorganic metal salt selected from the group consisting of aluminum nitrate, ammonium aluminum sulfate and potassium aluminum sulfate.

5. The agricultural chemical composition according to any one of claims 1 to 3, wherein the component (b) is one or more than one compound selected from the group consisting of:

0.001 to 100 parts by weight of a phosphorus acid compound represented by the following formula (I):

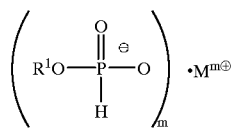

wherein $R^1$ represents an ethyl group, M represents an aluminum atom and m stands for 3;

0.01 to 300 parts by weight of chitosan;

0.001 to 100 parts by weight of an organic metal salt selected from the group consisting of magnesium lactate, aluminum lactate, calcium lactate, calcium propionate, aluminum acetate, calcium levulinate, calcium benzoate, magnesium citrate, calcium citrate, calcium salicylate and magnesium ethoxide; and 0.001 to 100 parts by weight of an inorganic metal salt selected from the group consisting of aluminum nitrate, ammonium aluminum sulfate and potassium aluminum sulfate.

6. The agricultural chemical composition according to any one of claims 1 to 3, wherein the component (b) is one or more than one compound selected from group consisting of 0.001 to 100 parts by weight of:

a fosetyl aluminum salt;

an organic metal salt selected from the group consisting of magnesium lactate, aluminum lactate, calcium lactate, calcium propionate, magnesium citrate and calcium citrate; and an inorganic metal salt selected from the group consisting of ammonium aluminum sulfate and potassium aluminum sulfate.

7. The agricultural chemical composition according to any one of claims 1 to 3, wherein the component (c) is included in the composition and is one or more than one compound selected from the group consisting of a plant growth regulator, a fungicide which is an inhibitor of ergosterol biosynthesis and mefluidide.

8. The agricultural chemical composition according to claim 4, wherein the component (c) is included in the composition and is one or more than one compound selected from the group consisting of a plant growth regulator, a fungicide which is an inhibitor of ergosterol biosynthesis and mefluidide.

9. The agricultural chemical composition according to claim 5, wherein the component (c) is included in the composition and is one or more than one compound selected from the group consisting of a plant growth regulator, a fungicide which is an inhibitor of ergosterol biosynthesis and mefluidide.

10. The agricultural chemical composition according to claim 5, wherein the component (c) is included in the composition and is one or more than one compound selected from the group consisting of a plant growth regulator, a fungicide which is an inhibitor of ergosterol biosynthesis and mefluidide.

11. The agricultural chemical composition according to any one of claims 1 to 3, wherein the component (c) is included in the composition and is one or more than one compound which is a plant growth regulator.

12. The agricultural chemical composition according to claim 4, wherein the component (c) is included in the composition and is one or more than one compound which is a plant growth regulator.

13. The agricultural chemical composition according to claim 5, wherein the component (c) is included in the composition and is one or more than one compound which is a plant growth regulator.

14. The agricultural chemical composition according to claim 6, wherein the component (c) is included in the composition and is one or more than one compound which is a plant growth regulator.

15. The agricultural chemical composition according to any one of claims 1 to 3, wherein the component (c) is included in the composition and is one or more than one compound selected from the group consisting of maleic hyrazide, a salt of maleic hydrazide, flurprimidol, abscisic acid, paclobutrazol, trinexapac-ethyl and prohexadione-calcium.

16. The agricultural chemical composition according to claim 4, wherein the component (c) is included in the composition and is one or more than one compound selected from the group consisting of maleic hyrazide, a salt of maleic hydrazide, flurprimidol, abscisic acid, paclobutrazol, trinexapac-ethyl and prohexadione-calcium.

17. The agricultural chemical composition according to claim 5, wherein the component (c) is included in the composition and is one or more than one compound selected from the group consisting of maleic hyrazide, a salt of maleic hydrazide, flurprimidol, abscisic acid, paclobutrazol, trinexapac-ethyl and prohexadione-calcium.

18. The agricultural chemical composition according to claim 6, wherein the component (c) is included in the composition and is one or more than one compound selected from the group consisting of maleic hyrazide, a salt of maleic hydrazide, flurprimidol, abscisic acid, paclobutrazol, trinexapac-ethyl and prohexadione-calcium.

19. The agricultural chemical composition according to any one of claims 1 to 3, wherein the component (c) is included in the composition and is one or more than one compound selected from the group consisting of maleic hydrazide and a salt of maleic hydrazide.

20. The agricultural chemical composition according to claim 4, wherein the component (c) is included in the composition and is one or more than one compound selected from the group consisting of maleic hydrazide and a salt of maleic hydrazide.

21. The agricultural chemical composition according to claim 5, wherein the component (c) is included in the composition and is one or more than one compound selected from the group consisting of maleic hydrazide and a salt of maleic hydrazide.

22. The agricultural chemical composition according to claim 6, wherein the component (c) is included in the composition and is one or more than one compound selected from the group consisting of maleic hydrazide and a salt of maleic hydrazide.

23. The agricultural chemical composition according to claim 1, wherein the component (a) is one or more than one compound selected from the group consisting of 4-(hydroxy(methyl)phosphinoyl)-DL-homoalanine and a salt thereof, and the composition is a crop selective herbicide composition.

24. The agricultural chemical composition according to claim 1 or claim 23, wherein the component (b) is one or more than one compound selected from the group consisting of 0.001 to 100 parts by weight of a phosphorus acid compound represented by the following formula (I):

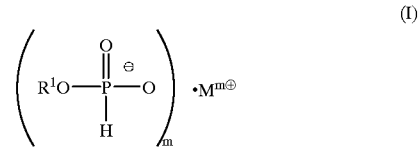

wherein $R^1$ represents a $C_{1-4}$ alkyl group, M represents a magnesium atom, a calcium atom, a barium atom or an aluminum atom and m stands for an integer equivalent to the positive valency of M;

0.01 to 300 parts by weight of a chitosan compound represented by the following formula (II):

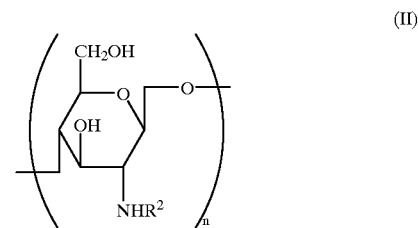

wherein n stands for an integer of 1 or greater and $R^2$ represents a hydrogen atom or an acetyl group; and 0.001 to 100 parts by weight of an organic acid metal salt selected from the group consisting of an aluminum salt and a calcium salt of an organic acid selected from the group consisting of lactic acid, propionic acid, acetic acid, levulinic acid, benzoic acid, citric acid and alginic acid with the proviso that magnesium acetate and calcium acetate are excluded when the component (a) contains N-(phosphonomethyl)glycine or a salt thereof, and aluminum acetylacetate.

25. The agricultural chemical composition according to claim 1 or claim 23, wherein the component (b) is one or more than one compound selected from the group consisting of 0.001 to 100 parts by weight of a phosphorus acid compound represented by the following formula (I):

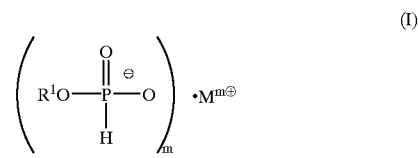

wherein $R^1$ represents an ethyl group, M represents an aluminum atom and m stands for 3;

0.01 to 300 parts by weight of chitosan; and 0.001 to 100 parts by weight of an organic metal salt selected from the group consisting of aluminum lactate, calcium lactate, calcium propionate, aluminum acetate, calcium acetate, calcium levulinate, calcium benzoate, calcium citrate, calcium alginate and aluminum acetylacetate.

26. The agricultural chemical composition according to claim 1 or claim 23, wherein the component (b) is one or more than one compound selected from the group consisting of 0.001 to 100 parts by weight of a fosetyl aluminum salt and an organic metal salt selected from the group consisting of aluminum lactate, aluminum acetate, calcium acetate and aluminum acetylacetate.

27. The agricultural chemical composition according to claim 1, wherein the component (c) is included in the composition and is one or more than one compound selected from the group consisting of atrazine, pyridate and clopyralid.

28. The agricultural chemical composition according to claim 23, wherein the component (c) is included in the composition and is one or more than one compound selected from the group consisting of atrazine, pyridate and clopyralid.

29. The agricultural chemical composition according to claim 24, wherein the component (c) is included in the composition and is one or more than one compound selected from the group consisting of atrazine, pyridate and clopyralid.

30. The agricultural chemical composition according to claim 25, wherein the component (c) is included in the composition and is one or more than one compound selected from the group consisting of atrazine, pyridate and clopyralid.

31. The agricultural chemical composition according to claim 26, wherein the component (c) is included in the composition and is one or more than one compound selected from the group consisting of atrazine, pyridate and clopyralid.

32. The agricultural chemical composition according to claim 1, wherein the component (c) is included in the composition and is one or more than one compound selected from the group consisting of atrazine and pyridate.

33. The agricultural chemical composition according to claim 23, wherein the component (c) is included in the composition and is one or more than one compound selected from the group consisting of atrazine and pyridate.

34. The agricultural chemical composition according to claim 24, wherein the component (c) is included in the composition and is one or more than one compound selected from the group consisting of atrazine and pyridate.

35. The agricultural chemical composition according to claim 25, wherein the component (c) is included in the composition and is one or more than one compound selected from the group consisting of atrazine and pyridate.

36. The agricultural chemical composition according to claim 26, wherein the component (c) is included in the composition and is one or more than one compound selected from the group consisting of atrazine and pyridate.

37. The agricultural chemical composition according to claim 1, wherein for component (b), components (i), (iii), (iv) and (v) are in amounts of 0.01 to 20 parts by weight and component (ii) is in an amount of 0.1 to 200 parts by weight; and component (c) is included in the composition and is in an amount of 1 to 50 parts by weight.

38. The agricultural chemical composition according to claim 1, wherein for component (b), components (i), (iii), (iv) and (v) are in amounts of 0.5 to 20 parts by weight and component (ii) is in an amount of 1 to 100 parts by weight; and component (c) is included in the composition and is in an amount of 1 to 50 parts by weight.

39. The agricultural chemical composition according to claim 1, wherein the component (c) is included in the composition and is being selected from the group consisting of maleic hydrazide, a salt of maleic hydrazide, uniconazole, flurprimidol, inabenfide, chlormequat chloride, dikegulac, ancymidol, abscisic acid, paclobutrazol, trinexapac-ethyl, prohexadione-calcium, choline chloride, triadimefor, triflumizole, pyrifenox, propiconazole, 2-(4-fluorophenyl)-1-(1H-1,2,4-trizol-1-yl)-3-trimethylsilyl-2-propanol, mefluidide, atrazine, pyridate and clopyralid.

40. The agricultural chemical composition according to claim 1, wherein the component (b) is said chitosan compound and n is 1 to 10000.

41. The agricultural chemical composition according to claim 40, wherein n is 1 to 1000 and $R^2$ is a hydrogen atom or a $C_1$–$C_{11}$ acyl group.

42. The agricultural chemical composition according to claim 1, wherein the component (b) is said isopropyl phosphate salt.

43. The agricultural chemical composition according to claim 1, wherein the component (a) is N-(phosphonomethyl) glycine and the component (b) is a metal salt selected from the group consisting of aluminum nitrate, aluminum ammonium sulfate, aluminum acetate, aluminum lactate, calcium formate, calcium citrate, calcium phosphinate, calcium lactate, calcium propionate, calcium salicylate, calcium acetate salt, calcium levulinate salt, calcium benzoate salt, fosetyl aluminum salt, fosetyl iron salt, a phosphonic acid monoisopropyl ester aluminum salt, fosetyl barium salt, magnesium lactate, magnesium ethoxide and magnesium citrate.

44. The agricultural chemical composition according to claim 1, wherein the component (a) is selected from the group consisting of N-(phosphonomethyl)glycine and 4-(hydroxy(methyl)phosphinoyl)-DL-homoalanine; and the component (b) is selected from the group consisting of a fosetyl aluminum salt and calcium propionate.

45. The agricultural chemical composition according to claim 1, wherein the component (a) is N-(phosphonomethyl) glycine and the compound (b) is phosphorus acid.

46. The agricultural chemical composition according to claim 1, wherein the component (a) is 4-(hydroxy(methyl) phosphinoyl)-DL-homoalanine, the component (b) is fosetyl aluminum salt and the component (c) is included in the composition and is atrazine.

47. The agricultural chemical composition according to claim 1, wherein the component (a) is 4-(hydroxy(methyl) phosphinoyl)-DL-homoalanine, the component (b) is chitosan and the component (c) is included in the composition and is atrazine.

48. The agricultural chemical composition according to claim 1, wherein the component (a) is N,N-bis (phosphonomethyl)glycine.

49. A method for retarding plant growth comprising applying to a plant an effective growth retarding amount of the plant retardant growth retardant composition according to claim 2.

50. A method for controlling the growth of undesired plants among crop plants comprising applying to a site on which crop plants are growing an effective herbicidal amount of the crop selective herbicide composition according to claim 3.

* * * * *